United States Patent
Uitterlinden et al.

(10) Patent No.: US 7,354,712 B2
(45) Date of Patent: Apr. 8, 2008

(54) ESTROGEN RECEPTOR ALLELES THAT ARE PREDICTIVE OF INCREASED SUSCEPTIBILITY TO BONE FRACTURE

(75) Inventors: Andreas Gerardus Uitterlinden, Poortugaal (NL); Johannes Petrus Thomas Maria Van Leeuwen, Amstelveen (NL); Huibert Adriaan Pieter Pols, Papendrecht (NL)

(73) Assignee: Century Technology, Inc., Wilmington, DE (US)

( * ) Notice: Subject to any disclaimer, the term of this patent is extended or adjusted under 35 U.S.C. 154(b) by 535 days.

(21) Appl. No.: 10/601,345

(22) Filed: Jun. 19, 2003

(65) Prior Publication Data
US 2005/0202435 A1 Sep. 15, 2005

Related U.S. Application Data

(60) Provisional application No. 60/469,618, filed on May 9, 2003, provisional application No. 60/466,963, filed on Apr. 30, 2003.

(51) Int. Cl.
*C12Q 1/68* (2006.01)
*C12P 19/34* (2006.01)
(52) U.S. Cl. .......................................... 435/6; 435/91.2
(58) Field of Classification Search .................... None
See application file for complete search history.

(56) References Cited

U.S. PATENT DOCUMENTS

| 4,529,593 | A | * | 7/1985 | Warrell et al. ............... 424/650 |
| 5,593,833 | A | | 1/1997 | Morrison et al. |
| 5,939,260 | A | | 8/1999 | Spector et al. |

FOREIGN PATENT DOCUMENTS

| WO | WO 94/03633 A1 | 2/1994 |
| WO | WO 97/40187 A1 | 10/1997 |

OTHER PUBLICATIONS

Aerssens et al. 2000 Osteoporos International vol. 11 p. 583.*
Kobayasi et al 2002 Maturitas vol. 41 p. 193.*
Van Meurs et al. 2003 Human Molecular Genetics vol. 12 p. 1745.*
Uitterlinden et al. 2001 Journal of Bone and Mineral Research vol. 16 p. 379.*
Wiling et al. 1998 Journal of Bone and Mineral Research vol. 13 p. 695.*
Chango, A., et al., "5,10-Methylenetetrahydrofolate Reductase Common Mutations, Folate Status and Plasma Homocysteine in Healthy French Adults of the Supplementation en Vitamines et Mineraux Antioxydants (SU.VI.MAX) Cohort," *British Journal of Nutrition* 84:891-896, 2000.
Christensen, B., et al., "Correlation of a Common Mutation in the Methylenetetrahydrofolate Reductase Gene With Plasma Homocysteine in Patients With Premature Coronary Artery Disease," *Arteriosclerosis, Thrombosis, and Vascular Biology* 17(3):569-573, Mar. 1997.
Cooper, G.S. and D.M. Umbach, "Are Vitamin D Receptor Polymorphisms Associated With Bone Density?, A Meta-Analysis," *J. Bone Miner. Res.* 11:1841-1849, 1996.
Goyette, P., et al., "Human Methylenetetrahydrofolate Reductase: Isolation of cDNA, Mapping and Mutation Identification," *Nature Genetics* 7:195-200, Jun. 1994.
Goyette, P., et al., "Gene Structure of Human and Mouse Methylenetetrahydrofolate Reductase (MTHFR)," *Mammalian Genome* 9:652-656, 1998.
Grant, S.F.A., et al., "Reduced Bone Density and Osteoporosis Associated With a Polymorphic Sp1 Binding Site in the Collagen Type Iα1 Gene," *Nature Genetics* 14:203-205, Oct. 1996.
Hofman, A., et al., "Determinants of Disease and Disability in the Elderly: The Rotterdam Elderly Study," *Eur. J. Epidemiol.* 7(4):403-422, Jul. 1991.
Houston, L.A., et al., "Vitamin D Receptor Polymorphism, Bone Mineral Density, and Osteoporotic Vertebral Fracture: Studies in a UK Population," *Bone* 18(3):249-252, 1996.
Ioannidis, J.P.A., et al., "Association of Polymorphisms of the Estrogen Receptor Alpha Gene With Bone Mineral Density and Fracture Risk in Women: A Meta-Analysis," *J. Bone Miner. Res.* 17(11):2048-2060, 2002 [Abstract].
Mann, V., et al., "A *COL1A1* Sp1 Binding Site Polymorphism Predisposes to Osteoporotic Fracture by Affecting Bone Density and Quality," *J. Clin. Invest.* 107(7):899-907, Apr. 2001.
Miyao, M., et al., "Association of Methylenetetrahydrofolate Reductase (MTHFR) Polymorphism With Bone Mineral Density in Postmenopausal Japanese Women," *Calcified Tissue Int'l* 66:190-194, 2000.
Moritsugu, K.P., et al., "Report of the Surgeon General's Workshop on Osteoporosis and Bone Health," *Proceedings of the Surgeon General's Workshop on Osteoporosis and Bone Health*, Washington, D.C., Dec. 12-13, 2002, pp. 1-55.
Morrison, N.A., et al., "Prediction of Bone Density From Vitamin D Receptor Alleles," *Nature* 367:284-287, 1994.
Ralston, S.H., "Genetic Markers of Bone Metabolism and Bone Disease," *Scand. J. Clin. Lab. Invest.* 57(Suppl. 227):114-121, 1997.
Ralston, S.H., "The Genetics of Osteoporosis," *Q.J. Med.* 90:247-251, 1997.
Uitterlinden, A.G., et al., "Interaction Between the Vitamin D Receptor Gene and Collagen Type Iα1 Gene in Susceptibility for Fracture," *J. Bone Miner. Res.* 16:379-385, 2001 [Abstract].

(Continued)

*Primary Examiner*—Ram R. Shukla
*Assistant Examiner*—Katherine Salmon
(74) *Attorney, Agent, or Firm*—Sheridan Ross P.C.

(57) ABSTRACT

In one aspect, the present invention provides methods of determining susceptibility to bone fracture in a mammalian subject, wherein the methods comprise analyzing nucleic acid molecules obtained from the mammalian subject to determine which of the P, p X, and x alleles of the estrogen receptor α gene are present, wherein the presence of a haplotype comprising the p and x alleles is indicative of an increased susceptibility to bone fracture. The present invention also provides kits for determining susceptibility to bone fracture in a mammalian subject.

7 Claims, 9 Drawing Sheets

OTHER PUBLICATIONS

Uitterlinden, A.G., et al., "A Large-Scale Population-Based Study of the Association of Vitamin D. Receptor Gene Polymorphisms With Bone Mineral Density," *J. Bone Miner. Res.* 11(9):1241-1248, 1996.

Uitterlinden, A.G., et al., "Relation of Alleles of the Collagen Type Iα1 Gene to Bone Density and the Risk of Osteoporotic Fractures in Postmenopausal Women," *New Engl. J. Med.* 338(15):1016-1021, Apr. 9, 1998.

Uitterlinden, A.G., et al., "Sp1 Binding Site Polymorphism in the COLIA1 Gene Is Associated With BMD: The Rotterdam Study," *Osteoporosis Int'l*, 6(1):124, PSu164, 1996 [Abstract].

Uitterlinden, A.G., Ph.D., et al., "Vitamin D Receptor Genotype Is Associated With Radiographic Osteoarthritis at the Knee," *J. Clin. Invest.* 100(2):259-263, 1997.

Van der Klift, M., et al., "The Incidence of Vertebral Fractures in Men and Women: The Rotterdam Study," *J. Bone Miner. Res.* 17(6):1051-1056, 2002 [Abstract].

White, C.P., et al., "Vitamin D Receptor Alleles Predict Osteoporotic Fracture Risk," *J. Bone Miner. Res.* 9(suppll):S263, 1994 [Abstract].

Willing, M., et al., "Bone Mineral Density and its Change in White Women: Estrogen and Vitamin D Receptor Genotypes and Their Interaction," *J. Bone Miner. Res.* 13(4):695-705, 1998 [Abstract].

\* cited by examiner

ACAGTATTTCAAATTACACATTATTCAAGTTATAAAAACTGATATCCAAGGGTTATGTGGCAATGA (forward primer):

CGTAAAAATTGAATTGTTATTTTTTGACACATGTTCTGTGTTGTCCATCAGTTCATCTGAGT

Pvu II RFLP (397 bp in front of exon2)

TCCAAATGTCCCCAGC (T/C) GTTTATGCTTTGTCTCTCTGTTTCCCAGAGACCCTGAGTGTGGTC

Xba I RFLP (351 bp in front of exon2)

T (A/G) GAGTTGGGGATGAGCATTGGTCTCTCTAATGGTTCTGAAATAATTGTATATTCCTGCAAAA

ACATTAAGTCTATTAGAACCAGCTAATTTCATTTTGTCATTTTTATAGGTAACATATTCTGGT (reverse primer):

GCAGGTAGTATGTTTTAAAAACAAGTTTGCAATAAACAATTCCCCTCAAGGTTAATATAATAG

GCAACACCTTTTGCTGCAACAGACGGCAAGAGGTAATGAAAGAT

*Fig.5.*

```
<<< Exon 7 >>        VDR1 (forward primer)
GGACGACATGTCCTGGACCTGTGGCAACCAAGACTACAAGTA
CCGCGTCAGTGACGTGACCAAAGG tatgcctagactccacct
cctggggagtcttttcagctcccagattctggc
              forward primer in intron 7)
tccacccgtcctggggtttggctccaatcagatacatgggag
ggagttaggcaccaacagggagagaagggcgagggtcagacc
catggggttggaggtgggtgggcggctcctcagc
                         Exon 8 >>
tctgcccgcagtacctggccattgtctctcacagcc GGACAC
AGCCTGGAGCTGATTGAGCCCCTCATCAAGTTCCAGGTGGGA
CTGAAGAAGCTGAACTTGCATGAGGAGGAGCATGTCCTGCTC
ATGGCCATCTGCATCGTCTCCCAG gtatggggccaggcagg
gaggagctcagggacctggggagcgggagagtatgaaggaca
aagacctgctgagggccagctgggcaacctgaagggagacgt
agcaaaaggagacacagataaggaaatacctactttgctggt
ttgcagagccctgtggtgtgtggacgctgaggtgcccctca
ctgccttagctctgccttgcagagtgtgcaggcgattcgta
gggggggattctgaggaactagataagcagggttcc
```

*Fig. 6A.*

Bsm I RFLP (in intron 8)

tggggccacagacaggcctgc(a/g)cattcccaatactcag
gctctgctcttgcgtgaactgggctcaacattcctgttattt
gaggtttcttgcgggcagggtacaaactttggagcctgaga
gatggttctgcctatatagtttacctgattgattttggaggc
aatgtgcagtgaccttgacctcttccgctggttagaggtga
gaagagggagaaaaggccgaagaggaagttattgtgaccttg
gggacatgatgtcggtgatgaggtccaagaggggcggccct
gcctcagcctgtgctagtggcctgtgcccagggatgctttcc
tggactggaggctcaaggaatggagatgggctcctctacccc
tgcccagccagccttctctcattcattcatccacttagcaac
aatttattgagcacctattaggtaccaggcactatgctaggt
actggggttcagcagcaaatgggacacaggctcctctcccat
gaagcttaggaggaaacattaaacaatgttatttaattatt
aattcctaacaaggcaagagttttaaaaataaagtaagtgat
gctacagaagggtagaatagaaggagggaagctgacgtggtc
tgggctacagaggtagagtgttgccaggaatggccttttgga
ggaagacctttaagctgttatccaaaggatcagtaagagtc
tggcaaagatagcagagcagagttccaagcagagggagcaca
gatgtgaaggctggtggccagagagcatggcgcatcgggacg
ctgagggatggacagagcatggacagggagcaaggccaggca
gggacagggccaggtgcgcccatggaaggacctaggtctgga

*Fig. 6B.* tcctaaatgcacggagaagtcactggagggctttgggggccag gcagtggtatcaccggtcagcagtcatagaggggtggcctag ggggtgctgccgttgagtgtctgtgtgggtgggggggt

Apa I RFLP (in intron 8)

ggtgggattgagcagtgagg(g/t)gcccagctgagagctcc tgtgccttcttctctat

Exon 9 >> Taq I RFLP (in exon 9)

ccccgtgcccacagATCGTCCTGGGGTGCAGGACGCCGCGCT
GAT(T/C)GAGGCCATCCAGGACCGCCTGTCCAACACACTGC
AGACGTACATCCGCTGCCGCCACCCGCCCCCGGGCAGCCACC
TGCTCTATGCCAAGATGATCCAGAAGCTAGCCGACCTGCGCA
GCCTCAATGAGGAGCACTCCAAGCAGTACCGCTGCCTCTCCT
TCCAGCCTGAGTGCAGCATGAAGCTA

*Fig. 6C.*

3'-UTR >>>

ACGCCCCTTGTGCTCGAAGTGTTTGGCAATGAGATCTCCtga ctaggacagcctgtggcggtgcctgggtggggctgctcctcc agggccacgtgccaggcccggggctggcggctactcagcagc cctcctcacccgtctggggttcagcccctcctctgccacct ccctatccacccagcccattctctcctgtccaacctaac ccctttcctgcgggcttttccccggt (reverse primer):

ccc ttgagacctcagccatgaggagttgctgtttgtttgaca aagaaacccaagtgggggcagagggcagaggctggaggcagg gccttgcccagagatgcctccaccgctgcctaagtggctgct gactgatgttgagggaacagacaggagaaatgcatccattcc tcagggacagagacacctgcacctcccccactgcaggcccc gcttgtccagcgcct...

SEQUENCE LISTING

<160> NUMBER OF SEQ ID NOS: 7

<210> SEQ ID NO 1
<211> LENGTH: 420
<212> TYPE: DNA
<213> ORGANISM: Homo Sapien

<400> SEQUENCE: 1

```
acagtatttt caaattacat tattcaagtt ataaaaactg atatccaggg ttatgtggca      60
atgacgtaaa aatttgaatt gttatttttt tgacacatgt tctgtgttgt ccatcagttc     120
atctgagttc caaatgtccc agcygtttta tgctttgtct ctgtttccca gagacctga     180 gtgtggtctr gagttgggat gagcattggt ctctaatggt tctgaaataa ttgtatattc     240
ctgcaaaaac attaagtcta ttagaaacca gctaatttca ttttgtcatt tttataggta     300
acatattctg gtgcaggtag tatgttttta aaacaagttt gcaataaaca atttcccctc     360
aaggttaata taataggcaa caccttttgc tgcaacagac ggcaagaggt aatgaaagat     420
```

<210> SEQ ID NO 2
<211> LENGTH: 2396
<212> TYPE: DNA
<213> ORGANISM: Homo Sapien

<400> SEQUENCE: 2

```
ggacgacatg tcctggacct gtggcaacca agactacaag taccgcgtca gtgacgtgac      60
caaaggtatg cctagactcc acctcctggg gagtcttttt cagctcccag attctggctc     120
cacccgtcct ggggtttggc tccaatcaga tacatgggag ggagttaggc accaacaggg     180
```

```
agagaagggc gagggtcaga cccatggggt tggaggtggg tgggcggctc ctcagctctg    240
cccgcagtac ctggccattg tctctcacag ccggacacag cctggagctg attgagcccc    300
tcatcaagtt ccaggtggga ctgaagaagc tgaacttgca tgaggaggag catgtcctgc    360
tcatggccat ctgcatcgtc tccccaggta tggggccagg cagggaggag ctcagggacc    420
tggggagcgg gagagtatga aggacaaaga cctgctgagg gccagctggg caacctgaag    480
ggagacgtag caaaaggaga cacagataag gaaataccta ctttgctggt ttgcagagcc    540
cctgtggtgt gtggacgctg aggtgcccct cactgccctt agctctgcct tgcagagtgt    600
gcaggcgatt cgtaggggga attctgagga actagataag cagggttcct ggggccacag    660
acaggcctgc rcattcccaa tactcaggct ctgctcttgc gtgaactggg ctcaacattc    720
ctgttatttg aggtttcttg cgggcagggt acaaaacttt ggagcctgag atggttct     780
gcctatatag tttacctgat tgattttgga ggcaatgtgc agtgacccct gacctcttcc    840
gctggttaga ggtgagaaga gggagaaaag gccgaagagg aagttattgt gaccttgggg    900
acatgatgtc ggtgatgagg tccaaagagg ggcggccctg cctcagcctg tgctagtggc    960
ctgtgcccag ggatgctttc ctggactgga ggctcaagga atggagatgg gctcctctac   1020
ccctgcccag ccagccttct ctcattcatt catccactta gcaacaattt attgagcacc   1080
tattaggtac caggcactat gctaggtact ggggttcagc agcaaatggg acacaggctc   1140
ctctcccatg aagcttagga ggaaacatta aacaaatgtt atttaattat taattcctaa   1200
caaggcaaga gttttaaaaa taagtaagt gatgctacag aagggtagaa tagaaggagg   1260
gaagctgacg tggtctgggc tacagaggta gagtgttgcc aggaatggcc ttttggagga   1320
agaccttta agctgttatc caaaggatca gtaagagtct ggcaaagata gcagagcaga   1380
gttccaagca gagggagcac agatgtgaag gctggtggcc agagagcatg gcgcatcggg   1440
acgctgaggg atggacagag catggacagg gagcaaggcc aggcagggac agggccaggt   1500
gcgcccatgg aaggacctag gtctggatcc taaatgcacg gagaagtcac tggagggctt   1560
tggggccagg cagtggtatc accggtcagc agtcatagag gggtggccta gggggtgctg   1620
ccgttgagtg tctgtgtggg tgggggtgg tgggattgag cagtgaggkg cccagctgag   1680
agctcctgtg ccttcttctc tatccccgtg cccacagatc gtcctggggt gcaggacgcc   1740
gcgctgatyg aggccatcca ggaccgcctg tccaacacac tgcagacgta catccgctgc   1800
cgccacccgc ccccgggcag ccacctgctc tatgccaaga tgatccagaa gctagccgac   1860
ctgcgcagcc tcaatgagga gcactccaag cagtaccgct gcctctcctt ccagcctgag   1920
tgcagcatga agctaacgcc ccttgtgctc gaagtgtttg gcaatgagat ctcctgacta   1980
ggacagcctg tggcggtgcc tgggtggggc tgctcctcca gggccacgtg ccaggcccgg   2040
ggctggcggc tactcagcag ccctcctcac ccgtctgggc gttcagcccc tcctctgcca   2100
cctcccctat ccacccagcc cattctctct cctgtccaac ctaacccctt tcctgcgggc   2160
ttttccccgg tcccttgaga cctcagccat gaggagttgc tgtttgtttg acaaagaaac   2220
ccaagtgggg gcagagggca gaggctggag gcagggcctt gcccagagat gcctccaccg   2280
ctgcctaagt ggctgctgac tgatgttgag ggaacagaca ggagaaatgc atccattcct   2340
cagggacaga gacacctgca cctcccccca ctgcaggccc cgcttgtcca gcgcct       2396
```

<210> SEQ ID NO 3
<211> LENGTH: 21
<212> TYPE: DNA

-continued

```
<213> ORGANISM: Artificial Sequence
<220> FEATURE:
<223> OTHER INFORMATION: Oligonucleotide PCR Primer

<400> SEQUENCE: 3
gatatccagg gttatgtggc a                                              21

<210> SEQ ID NO 4
<211> LENGTH: 27
<212> TYPE: DNA
<213> ORGANISM: Artificial Sequence
<220> FEATURE:
<223> OTHER INFORMATION: Oligonucleotide PCR Primer

<400> SEQUENCE: 4
aggtgttgcc tattatatta accttga                                        27

<210> SEQ ID NO 5
<211> LENGTH: 30
<212> TYPE: DNA
<213> ORGANISM: Artificial Sequence
<220> FEATURE:
<223> OTHER INFORMATION: Oligonucleotide PCR Primer

<400> SEQUENCE: 5
caaccaagac tacaagtacc gcgtcagtga                                     30

<210> SEQ ID NO 6
<211> LENGTH: 25
<212> TYPE: DNA
<213> ORGANISM: Artificial Sequence
<220> FEATURE:
<223> OTHER INFORMATION: Oligonucleotide PCR Primer

<400> SEQUENCE: 6
tttggctcca atcagataca tggga                                          25

<210> SEQ ID NO 7
<211> LENGTH: 24
<212> TYPE: DNA
<213> ORGANISM: Artificial Sequence
<220> FEATURE:
<223> OTHER INFORMATION: Oligonucleotide PCR Primer

<400> SEQUENCE: 7
gcaactcctc atggctgagg tctc                                           24
```

ESTROGEN RECEPTOR ALLELES THAT ARE PREDICTIVE OF INCREASED SUSCEPTIBILITY TO BONE FRACTURE

CROSS-REFERENCES TO RELATED APPLICATIONS

This application claims the benefit of U.S. Provisional Application No. 60/466,963, filed Apr. 30, 2003, and U.S. Provisional Application No. 60/469,618, filed May 9, 2003.

FIELD OF THE INVENTION

The present invention relates to methods for determining susceptibility to bone fracture in a subject, methods of treating a subject to reduce the risk of bone fracture, methods of formulating a treatment regimen to decrease the risk of bone fracture, and kits for use in determining susceptibility to bone fracture.

BACKGROUND OF THE INVENTION

Osteoporosis is characterized by low bone mineral density (BMD), deterioration of the microarchitecture of bone and subsequent increased fracture. Twin and family studies have suggested that BMD has a strong genetic component, besides being influenced by nutritional and life-style factors. Osteoporosis is regarded as a complex genetic trait, which means that variants of several genes underlie the variability of the phenotype. Among the candidate genes in relation to BMD are the genes for collagen type IA1 (COLIA1), the Vitamin D receptor (VDR) and the estrogen receptor α (ERα). ERα is also known as estrogen receptor I (ESR I). Polymorphisms in the genes for the VDR and the ERα have been examined in relation to BMD. Although contrary reports have been published, two meta-analyses have shown a weak relation between the VDR gene and BMD. We and others have found a significant association between VDR polymorphisms and fracture risk while other studies could not confirm such an association. Also contrary reports regarding the contribution of polymorphisms in the ERα gene to BMD and fracture risk have been published. A recent meta-analysis has shown a relation between the ERα gene and BMD and fracture risk.

The vitamin D receptor gene (12q12) comprises inherited polymorphisms between exon 7 and 3' UTR of the VDR gene. These alleles are denoted B/b, A/a and T/t for restriction enzyme sites BsmI, ApaI and TaqI respectively (or enzymatic or chemical procedures having similar specificity), where a lower case letter denotes the presence of a wild type restriction site which is capable of being cleaved, and a capital letter denotes the presence of a mutant restriction enzyme site which is not capable of being cleaved by the relevant enzyme. For the purposes of the present invention, determination of which alleles are present in a particular gene may be referred to as determining the genotype of a subject for a particular gene. It is apparent from the above that each copy of the vitamin D receptor gene comprises a specific combination of the three alleles, this combination being referred to as the haplotype of the gene. For example, the haplotype may be baT, indicating the presence of cleavable BsmI and ApaI sites, and a non-cleavable TaqI site. Direct haplotyping of the VDR gene has allowed five different haplotypes to be determined, of which three are common.

Likewise the estrogen receptor α gene (also known as estrogen receptor I) has alleles denoted P/p and X/x for restrictions sites PvuII and XbaI respectively (or enzymatic or chemical procedures having similar specificity), where a lower case letter denotes the presence of a wild type restriction site which is capable of being cleaved, and a capital letter denotes the presence of a mutant restriction enzyme site which is not capable of being cleaved by the relevant restriction enzyme. For the purpose of the present invention, determination of which alleles are present in a particular gene may be referred to as determining the genotype of a subject for a particular gene. It is apparent from the above that each copy of the estrogen receptor α gene comprises a specific combination of the alleles, this combination is referred to as the haplotype of the gene. For example, the haplotype may be px, indication the presence of cleavable PvuI and XbaI sites. Direct haplotyping of the ERα gene has allowed three different haplotypes to be determined.

VDR and ERα are interesting genes because several interactions between the vitamin D and estrogen endocrine system have been described. 1,25-Dihydroxyvitamin $D_3$ (1,25-$(OH)_2D_3$) and 17β-estradiol ($E_2$) have a mutual effect on their biosynthesis and receptor expression. Also some genetic studies found an interaction between ERα and VDR genotypes with respect to BMD. Suarez et al. found an interactive effect of ERα and VDR gene polymorphisms on growth in infants.

So far most genetic studies on osteoporosis have focused on BMD as the primary endpoint and not on the clinically more relevant endpoint of fractures. In contrast, the invention disclosed in the present application utilizes the unexpected association between specific ERα and VDR genotypes and the most typical osteoporotic fracture, the vertebral fracture.

SUMMARY OF THE INVENTION

In a first aspect, the present invention provides methods for determining susceptibility to bone fracture in a mammalian subject comprising at least one estrogen receptor α gene comprising a PvuII site and a XbaI site, wherein the PvuII site can exist as a P or p allelic form, and the XbaI site can exist as an X or x allelic form, wherein the method comprises analyzing nucleic acid molecules (e.g., genomic DNA) obtained from the mammalian subject to determine which of the P, p X, and x alleles of the estrogen receptor α gene are present, wherein the presence of a haplotype comprising the p and x alleles is indicative of an increased susceptibility to bone fracture.

In some embodiments the method comprises analyzing nucleic acid molecules of a mammalian subject to determine the presence of the px haplotype of the estrogen receptor α gene, wherein the presence of said px haplotype is indicative of an increased susceptibility to bone fracture. In some embodiments, the method further comprises analyzing nucleic acid molecules of a mammalian subject to determine whether an allele of the vitamin D receptor gene is present which allele is indicative of an increased susceptibility to bone fracture. In some embodiments, the method comprises analyzing nucleic acid molecules of a mammalian subject to determine which of the B/b, A/a and T/t alleles of the BsmI, ApaI and TaqI sites of the vitamin D receptor gene are present, wherein the presence of a haplotype comprising at least of one of the baT alleles is indicative of an increased susceptibility to bone fracture. The method may comprise determining whether more than one of the above alleles is present. The subject may be further classified as heterozygous or homozygous for one or more of these alleles. Preferably, the method comprises the additional step of determining whether the allele(s) present are associated with risk of bone damage, wherein presence of the b, a or T alleles is associated with increased risk of bone damage. Homozygosity for the a or b allele may further increase the susceptibility to bone damage in a subject, while homozygosity for the t allele may further decrease susceptibility. Preferably, said method comprises determining whether the haplotype of the subject is associated with risk of bone damage, wherein the haplotype baT is associated with high risk of bone damage. A subject homozygous for said haplotype may be at higher risk of bone damage than those heterozygous for the haplotype.

In some embodiments, the method comprises analyzing nucleic acid molecules of a mammalian subject to determine the presence of the baT haplotype of the vitamin D receptor gene, wherein the presence of said baT haplotype is indicative of an increased susceptibility to bone fracture. In some embodiments the method further comprises determining the copy number of the P/p or X/x alleles of the estrogen receptor α gene and/or the B/b, A/a or T/t alleles of the vitamin D receptor gene.

In other embodiments, the method comprises comparing the allele(s) present in the mammalian subject with genotypes of the estrogen receptor α or vitamin D receptor genes having known degrees of risk of bone fracture.

In some embodiments the method is performed in vitro.

In some embodiments the method is performed on a blood or tissue sample of a subject.

In a second aspect of the invention there is provided methods of treating a mammalian subject to prevent or reduce the risk of bone fracture, wherein the mammalian subject comprises at least one estrogen receptor α gene comprising a PvuII site and a XbaI site, wherein the PvuII site can exist as a P or p allelic form, and the XbaI site can exist as an X or x allelic form, the methods each comprising analyzing nucleic acid molecules obtained from the mammalian subject to determine which of the P, p, X and x alleles of the PvuII and XbaI sites of the estrogen receptor α gene are present, wherein the presence of a haplotype comprising the p and x alleles is indicative of an increased susceptibility to bone fracture, and treating the mammalian subject to reduce the risk of bone fracture if the subject has a haplotype comprising the p and x alleles.

In some embodiments the method further comprises analyzing nucleic acid molecules of a mammalian subject to determine the presence of the px haplotype of the estrogen receptor α gene, wherein the presence of the px haplotype is indicative of an increased susceptibility to bone fracture.

In some embodiments the method further comprises analyzing nucleic acid molecules of a mammalian subject to determine which of the B/b, A/a and T/t alleles of the BsmI, ApaI and TaqI sites of the vitamin D receptor gene are present, wherein the presence of a haplotype comprising at least one of the baT alleles is indicative of an increased susceptibility to bone fracture. In some embodiments the method further comprises analyzing nucleic acid molecules of a mammalian subject to determine the presence of the baT haplotype of the vitamin D receptor gene, wherein the presence of the baT haplotype is indicative of an increased susceptibility to bone fracture.

In some embodiments the method further comprises determining the copy number of the P/p or X/x alleles of the estrogen receptor α gene and/or the B/b, A/a or T/t alleles of the vitamin D receptor gene.

In some embodiments the method comprises comparing the alleles present in the mammalian subject with genotypes of the estrogen receptor α gene and/or vitamin D receptor gene having known degrees of risk of bone fracture.

In some embodiments of the method suitable treatments include modifications to lifestyle, regular exercise, changes in diet or pharmaceutical preparations.

In some embodiments of the method the mammalian subject is a human.

In some embodiments of the method the mammalian subject is female.

In a third aspect of the invention there is provided methods of formulating a treatment regimen to decrease the risk of bone fracture in a mammalian subject, wherein the methods each comprise analyzing nucleic acid molecules of a mammalian subject to determine whether a px haplotype of an estrogen receptor α gene is present, wherein said haplotype is associated with risk of bone fracture, and formulating a treatment regimen to decrease the risk of bone fracture in the mammalian subject.

In some embodiments the method further comprises analyzing nucleic acid molecules of a mammalian subject to determine the presence of the baT haplotype of the vitamin D receptor gene, wherein said haplotype is associated with risk of bone fracture, and formulating a treatment regimen to decrease the risk of bone fracture based on said haplotype.

In some embodiments the method further comprises comparing the alleles present in the mammalian subject with genotypes of the estrogen receptor α gene and/or vitamin D receptor gene having known degrees of risk of bone fracture.

In some embodiments the method comprises administering an appropriate treatment, such as modifications to lifestyle, regular exercise, changes in diet or pharmaceutical preparations.

In a fourth aspect of the invention there is provided methods of determining susceptibility to bone fracture in a mammalian subject, wherein the methods each comprise the step of utilizing a kit to determine whether a px haplotype of an estrogen receptor α gene is present in a mammalian subject, wherein said kit comprises (i) one or more nucleic acid primer molecules for amplification of a portion of the estrogen receptor a gene, (ii) means for determining whether the px haplotype of said gene is present, and (iii) means for indicating a correlation between the presence of the px haplotype and risk of bone fracture, and wherein the presence of the px haplotype in the mammalian subject is indicative of susceptibility to bone fracture.

The association between the presence of the px haplotype and susceptibility to bone fracture is independent of BMD. In some embodiments the method further comprises the step of determining whether the baT haplotype of the vitamin D receptor gene is present in the mammalian subject, said kit further comprising (i) one or more nucleic acid primer molecules for amplification of a portion of the vitamin D receptor gene, (ii) means for determining whether the baT haplotype of the vitamin D receptor gene is present and (iii) means for indicating a correlation between the presence of the baT haplotype and risk of bone fracture.

In a fifth aspect of the invention there is provided a kit for determining susceptibility to bone fracture in a subject, said kit comprising (i) one or more nucleic acid primer molecules for amplification of a portion of an estrogen receptor α gene, (ii) means for determining whether a px haplotype of said gene is present; and (iii) means for indicating a correlation between the presence of said haplotype and risk of bone fracture.

In some embodiments the kit further comprises (i) one or more nucleic acid primer molecules for amplification of a portion of a vitamin D receptor gene, (ii) means for determining whether a baT haplotype of the vitamin D receptor gene is present, and (iii) means for indicating a correlation between the presence of the baT haplotype and risk of bone fracture.

In some embodiments of the first to fifth aspects the haplotype of the estrogen receptor α gene is determined by amplification of a portion of the first intron of the estrogen receptor α gene, followed by restriction enzyme digestion; or any other technique suitable for determining the genotype of the subject.

In some embodiments of the first to fifth aspects the haplotype of the vitamin D receptor is determined by amplification of a portion of the vitamin D receptor gene between exon 7 and the 3' untranslated region (UTR), followed by restriction enzyme digestion; or any other technique suitable for determining the genotype of the subject.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying tables and drawings, wherein:

FIG. 5 shows the nucleic acid sequence of part of intron I/exon 2 of the human Estrogen receptor α gene containing PvuII and xbaI polymorphisms. Nucleic acid sequences to which PCR primers anneal are underlined. The nucleic acid sequence of this portion of the estrogen receptor α gene is also shown in SEQ ID NO:1.

FIG. 6 shows the nucleic acid sequence of the 3' part of the human VDR gene containing BsmI, ApaI, and TaqI RFLP's polymorphic sites. The nucleic acid sequences to which PCR primers anneal are underlined. The nucleic acid sequence of this portion of the human VDR gene is also shown in SEQ ID NO:2.

DETAILED DESCRIPTION OF THE PREFERRED EMBODIMENT

Figure 1:
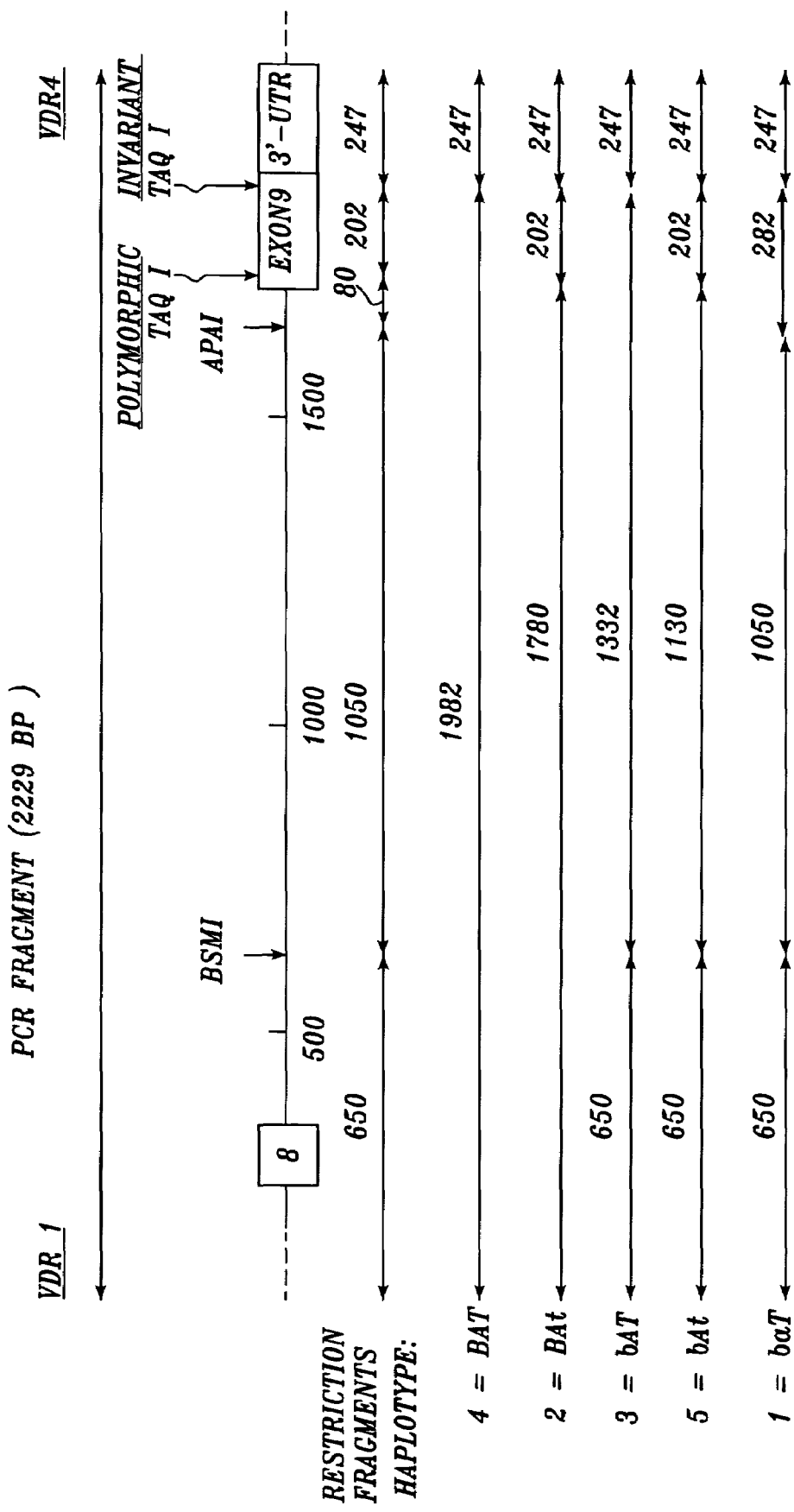
FIG. 1 shows VDR gene: direct molecular haplotyping. For details see Example 1.

Unless specifically defined herein, all terms used herein have the same meaning as they would to one skilled in the art of the present invention. Practitioners are particularly directed to Sambrook et al. (1989) *Molecular Cloning: A Laboratory Manual*, 2$^{nd}$ ed., Cold Spring Harbor Press, Plainsview, N.Y. (1989), and Ausubel et al., *Current Protocols in Molecular Biology* (Supplement 47), John Wiley & Sons, New York (1999), for definitions and terms of the art.

As used herein, the following terms have the meanings defined below: Estrogen receptor α (abbreviated as ERα) is a nuclear hormone receptor protein that binds estrogen and is thereby activated and binds to specific sequences of nuclear DNA which serve as on-off switches for transcription within the cell nucleus. Representative ERα genes that are analyzed in the practice of the present invention hybridize under conditions of 1.0×SSC, 0.5% SDS, at 30° C. for 30 minutes to the portion of the representative ERα gene set forth in SEQ ID NO:1. Some ERα genes that are analyzed in the practice of the present invention hybridize under conditions of 1.0×SSC, 0.5% SDS, at 45° C. for 30 minutes to the portion of the representative ERα gene set forth in SEQ ID NO:1. Some ERα genes that are analyzed in the practice of the present invention hybridize under conditions of 1.0×SSC, 0.5% SDS, at 60° C. for 30 minutes to the portion of the representative ERα gene set forth in SEQ ID NO:1. The ability to hybridize under the foregoing conditions can be determined, for example, by first hybridizing the nucleic acid molecules under low stringency conditions (e.g., 6×SSC, 0.5% SDS, at 25° C. for 12 hours), then incubating the hybridized nucleic acid molecules under the stated conditions (e.g., 1.0×SSC, 0.5% SDS, at 30° C. for 30 minutes).

There is a polymorphism at position 397 of the nucleotide sequence (numbered from the transcriptional start site) of the ERα gene. The polymorphism consists of a substitution of a C residue at position 397 of the sequence with a T residue. The genetic polymorphism is denoted "C397T" where the number refers to the position of the polymorphism with respect to the nucleotide sequence; the "C" is the nucleotide residue present in the reference or wild type sequence; and the "T" is the nucleotide residue present at that position in the variant sequence. There is a polymorphism at position 351 of the nucleotide sequence of the ERα gene. The polymorphism consists of a substitution of a G residue at position 351 for the sequence provided in SEQ ID NO:1 with a A residue. The genetic polymorphism is denoted "G351A" where the number refers to the position of the polymorphism with respect to the nucleotide sequence; the "G" is the nucleotide residue present in the reference or wild type sequence; and the "A" is the nucleotide residue present at that position in the variant sequence.

As used herein, the term "VDR gene" refers to a gene coding for the Vitamin D receptor.

As used herein, the term "bone damage" refers to any form of structural damage including fractures, break or chips. The term may also include biological degradation or deterioration of bone. Typically, the term "bone damage" does not include low bone mineral density. This is in line with the finding that risk of bone damage is independent of bone mineral density. Fracture may be defined as the clinically most important endpoint, and thus the method of the first aspect of the invention preferably relates to a method for determining risk of fracture independent of bone mineral density. Although such bone damage will usually be the result of osteoporosis, it is irrelevant for the purposes of the present invention whether a subject has first been diagnosed as having osteoporosis or low bone mineral density.

As used herein, the terms "risk of bone damage" and "susceptibility to bone damage" are used interchangeably and such risk or susceptibly is independent of bone mineral density. The present invention enables the identification of those individuals susceptible to bone fracture, and the development of therapeutic or preventative measures. For example, those at risk may avoid damage by modifying their lifestyle and implementing bone strengthening measures, such as regular exercise and a healthy diet, or by taking medicaments which reduce the risk of damage. Exemplary, art-recognized strategies for the prevention and/or treatment of individuals who are at increased risk of bone fracture are described in: DeSantis, A. and A. Buchman, "Current and Emerging Therapies in Osteoporosis," *Expert Opin. Pharmacother.* 3(7):835-843, 2002; Whitfield, J. A., et al., "Bone Growth Stimulators. New Tools for Treating Bone Loss and Mending Fractures," *Vitam. Horm.* 65:1-80, 2002; Lane, J. M., et al., "Medical Management of Osteoporosis," Institute for Biological Sciences, National Research Council of Canada, Ottawa, Ontario Canada, *Instr. Course Lect.* 52:785-789, 2003; Kim, I., "Osteoporosis in Aging-Challenges and Opportunities," *J. Okla. State Med. Assoc.* 96(3): 143-146, 2003; Body, J. J., "Management of Primary Osteoporosis," *Acta Clin. Belg.* 57(5):277-283, 2002.

In one aspect, the present invention provides methods for determining susceptibility to bone fracture in a mammalian subject comprising at least one estrogen receptor α gene comprising a PvuII site and a XbaI site, wherein the PvuII site can exist as a P or p allelic form, and the XbaI site can exist as an X or x allelic form, wherein the method comprises analyzing nucleic acid molecules (e.g., genomic DNA) obtained from the mammalian subject to determine which of the P, p X, and x alleles of the estrogen receptor α gene are present, wherein the presence of a haplotype comprising the p and x alleles is indicative of an increased susceptibility to bone fracture.

In some embodiments, the method further comprises analyzing nucleic acid molecules of a mammalian subject to determine whether an allele of the vitamin D receptor gene is present which allele is indicative of an increased susceptibility to bone fracture. In some embodiments, the method comprises analyzing nucleic acid molecules of a mammalian subject to determine which of the B/b, A/a and T/t alleles of the BsmI, ApaI and TaqI sites of the vitamin D receptor gene are present, wherein the presence of a haplotype comprising at least of one of the baT alleles is indicative of an increased susceptibility to bone fracture.

The determination that an allele of a polymorphism in an estrogen receptor α gene and/or a Vitamin D receptor gene is associated with an increased or decreased susceptibility to bone damage may be performed using standard statistical analyses in a population of subjects, as described, for example in the "statistical analysis" section. An exemplary method for determining the presence of one or more alleles associated with an increased or a decreased susceptibility to bone damage is present in a subject is described in detail below. An exemplary haplotype is the ERα haplotype 1 (px) of the estrogen receptor a and the VDR haplotype 1 (baT) of the VDR receptor. The estrogen receptor α gene comprises an inherited polymorphism at positions 397 and 351 of a nucleotide sequence of the ERα. The sequence of the estrogen receptor α gene and methodology on how to identify the C397T and G351A polymorphisms have been previously described.

The present invention is based upon the surprising observation of a correlation between the presence of the T allele at position 397 and/or the A allele at position 351 of the estrogen receptor α gene and the susceptibility to/or risk of bone fracture in those subjects having the polymorphisms independent of BMD. A subject having the estrogen receptor a T allele and the A allele in addition to the VDR haplotype 1 (baT) shows a higher risk of fracture compared to a subject having the estrogen receptor a C and G alleles and a haplotype of 2 (BAt) or 3 (bAT) for the VDR polymorphism.

These results could not be predicted as previous studies have shown that the fracture risk is dependent on bone mineral density. This fact is borne out by the results presented herein, where those individuals having the highest risk of bone fracture are those not having low bone mineral density. By screening for the alleles of the estrogen receptor α gene, and/or the VDR gene susceptibility to bone damage may be assessed without the need for an analysis of bone mineral density.

In some embodiments there are provided methods for determining susceptibility to bone damage in a subject comprising determining the presence of T allele of the C397T polymorphism of the estrogen receptor α gene and/or the A allele of the G351A polymorphism of the estrogen receptor α gene. This fact is confirmed by the result presented herein, that those individuals at highest risk of bone damage have both polymorphisms. Thus, some embodiments provide methods for determining susceptibility to bone damage in a subject, comprising determining the presence of the T allele of the C397T polymorphism of the estrogen receptor α gene and the A allele of the G351A polymorphism of the estrogen receptor α gene, wherein the presence of at least one copy of the T allele of the C397T polymorphism and at least one copy of the A allele of the G351A polymorphism of the estrogen receptor α gene in the subject is indicative of an increased susceptibility to bone fracture independent of bone mineral density.

Typically, the method of the first aspect of the present invention comprises analysis of polymorphisms in estrogen receptor α gene to determine susceptibility to bone damage. The method may include analysis of DNA, and/or RNA, to determine which allele of a polymorphism is present. The method may include determining whether one or more particular alleles are present. The method may further comprise determining whether subjects are homozygous or heterozygous for alleles of the estrogen receptor a gene.

Preferably, the method of the first aspect of the present invention further comprises analyzing nucleic acid molecules of a mammalian subject to determine whether an allele of the Vitamin D receptor is present which allele is indicative of an increased susceptibility to bone fracture. This may be performed by comparing the alleles present in a subject with those known to be associated with risk of bone damage. For example, a visual aid detailing alleles and the relative risk of bone damage associated therewith may be used to determine whether the genotype or phenotype of the subject is associated with a high or low risk of bone damage.

The methods of the present invention may be performed in vitro. Preferably, the method is performed on a tissue or fluid sample removed from the body of the subject. Thus, the present invention relates to a non-invasive diagnostic method, the results of which provide an indication of susceptibility to bone fracture but do not lead to a diagnosis upon which an immediate medical decision regarding treatment can be made.

The present invention may be performed on any living subject for which it is desirable to determine risk of bone fracture. Most preferably, the subject is a human, preferably a female.

The present invention may be performed using any suitable method known in the art. Preferably, a tissue or fluid sample is first removed from a subject. Examples of suitable samples include blood, mouth or cheek cells, and hair samples containing roots. Other suitable samples would be known to the person skilled in the art. The nucleic acid molecules are extracted from the sample, using any suitable method. For example the nucleic acid molecules may be extracted using the techniques described in Sambrook et al (Molecular Cloning—A Laboratory Manual, Cold Spring Harbor Laboratory Press). Determination of the genotype or phenotype of a subject may then be carried out using the extracted nucleic acid molecules, employing any suitable technique, including, for example, Southern blot analysis followed by restriction enzyme digestion; PCR amplification followed by restriction enzyme digestion and, optionally, separation of digestion products by gel electrophoresis; sequencing of a relevant gene fragment by any suitable method; visualization of heteroduplex patterns, for example on PAA or agarose gels, where different patterns may indicate the presence of one or more specific alleles; separation of DNA fragments using denaturing gradient gels, wherein the degree of separation will depend upon the presence or absence of one or more polymorphic restriction sites; separation using SSCP analysis, the patterns of which will depend upon the presence or absence of one or more polymorphic restriction sites, use of allele specific oligonucleotides, hybridization patterns of which some will be specific for various combinations of alleles; methods such as OLA, Taqman or dot-bloting for the detection of known mutations; visualization of DNA sites using fluorescent labeled probes for alleles of interest; and RFLP analysis. Other suitable methods will be known to persons skilled in the art.

Where it is desirable to use particular restriction enzymes in performing the present invention, the skilled person will understand that enzymatic or chemical procedures having similar specificities may also be used. For example, restriction enzymes having similar specificity (isoschizomers) to those described herein may be used, or chemical degradation procedures with DNA or RNA cutting specificity.

Other techniques suitable for determining the genotype or phenotype of a subject may be used in the present invention.

Amplification is preferably carried out by polymerase chain reaction (PCR) techniques, to produce copies of the amplified region, where the fragment is of the estrogen receptor α gene, the fragments are at least about 20, preferably at least about 50, about 70, about 100, about 150, or about 200 bases in length. Where the fragment to be amplified is of the VDR gene, PCR primers may be selected to amplify a fragment which is at least about 20, preferably at least about 50, about 70, about 100, about 150, or about 200 bases in length.

Exemplary PCR primers are at least about 10 nucleotides in length, preferably at least about 15 nucleotides or at least 20 nucleotides in length, and are complementary to any stretch of at least about 10 nucleotides of the sequence to be amplified. PCR techniques are well know in the art, and it is within the ambit of the skilled person to identify primers for amplification of the appropriate region of the above genes, namely the first intron of the estrogen receptor α gene and the region from exon 7 to the 3' UTR of the VDR gene. A preferred technique is single base extension, and for this method it is only necessary to amplify a fragment including the polymorphic site. Thus, amplification of the region immediately surrounding the C397T and G351A polymorphic site is necessary. Exemplary PCR techniques are described in EP-A-0200362 and EP-A-0201184.

In a preferred feature of the first aspect, there is provided a method for determining susceptibility to bone fracture in a subject, said method comprising amplifying a fragment comprising a portion of the first intron of the estrogen receptor a gene, and determining which allele(s) in the estrogen receptor α gene is/are present. Primers suitable for amplification of said portion of the estrogen receptor α gene would be readily available to a person skilled in the art. Examples for such primers include:

```
SEQ ID NO:3:  5'-GATATCCAGGGTTATGTGGCA-3'

SEQ ID NO:4:  5'-AGGTGTTGCCTATTATATTAACCTTGA-3'
```

To determine which allele of the VDR gene is present, at least a portion of the region from exon 7 to 3' UTR of the VDR may be amplified followed by the determination of the presence of the BsmI, ApaI and TaqI sites. Suitable primers include:

```
SEQ ID NO:5   5'-CAACCAAGACTACAAGTACCGCGTCAGTGA-3'
              and/or

SEQ ID NO:6   5'-TTTGGCTCCAATCAGATACATGGGA-3'

SEQ ID NO:7   5'-GCAACTCCTCATGGCTGAGGTCTC-3'
```

In a second aspect of the invention there is provided methods of treating a mammalian subject to prevent or reduce the risk of bone fracture, wherein the mammalian subject comprises at least one estrogen receptor α gene comprising a PvuII site and a XbaI site, wherein the PvuII site can exist as a P or p allelic form, and the XbaI site can exist as an X or x allelic form, the methods each comprising analyzing nucleic acid molecules obtained from the mammalian subject to determine which of the P, p, X and x alleles of the PvuII and XbaI sites of the estrogen receptor α gene are present, wherein the presence of a haplotype comprising the p and x alleles is indicative of an increased susceptibility to bone fracture, and treating the mammalian subject to reduce the risk of bone fracture if the subject has a haplotype comprising the p and x alleles.

In some embodiments the method further comprises analyzing nucleic acid molecules of the mammalian subject to determine which of the B/b, A/a and T/t alleles of the BsmI, ApaI and TaqI sites of the vitamin D receptor gene are present, wherein the presence of a haplotype comprising at least one of the baT alleles is indicative of an increased susceptibility to bone fracture. In some embodiments the method further comprises analyzing nucleic acid molecules of the mammalian subject to determine the presence of the baT haplotype of the vitamin D receptor gene, wherein the presence of the baT haplotype is indicative of an increased susceptibility to bone fracture.

In some embodiments the subject is diagnosed as being at risk of bone fracture, preferably using the method of the first aspect of the invention. In this aspect the reduction in risk of bone fracture includes any means of reducing risk of bone fracture in a subject.

Therapy may be in the form of preventative or palliative care. A preferred method of treatment is prescribing or administering an agent that reduces the susceptibility of a subject to bone fracture. For example, the treatment may comprise prescribing or administering Fosamax® (sodium alendronate) or Fosteo® (parathyroid hormone) or anabolic steroids, bisphosphonates, vitamin D preparations or other treatments known to those skilled in the art. Other suitable treatment which may be prescribed or administered alongside Fosamax or Fosteo, or as an alternative thereto, treatment also includes modifications to lifestyle, regular exercise and changes in diet to strengthen bones, and hormone therapy. Other suitable treatments including pharmaceutical preparations to reduce bone loss as known to physicians and persons skilled in the art. Examples include anabolic steroids, bisphosphonates, vitamin D preparations, calcium supplements and Hormone Replacement Therapy.

Administration of the medicament is accomplished by any effective route, e.g., orally or parenteral. Methods for parenteral delivery include topical, intra-arterial, subcutaneous, intramedullary, intravenous, or intranasal administration. Oral administration followed by subcutaneous injection would be the preferred routes of uptake, also long acting immobilizations would be used. In addition to the active ingredients, these medicaments may contain suitable pharmaceutically acceptable carriers comprising excipients and other compounds that facilitate processing of the active compounds into preparations which can be used pharmaceutically. Further details of techniques for formulation and administration may be found in the latest edition of "Remington's Pharmaceutical Sciences" (Mack Publishing Co, Easton Pa.).

Medicaments for oral administration can be formulated using pharmaceutically acceptable carriers well known in the art, in dosages suitable for oral administration. Such carriers enable the pharmaceutical compositions to be formulated as tablets, pills, dragees, capsules, liquids, gels, syrups, slurries, suspensions, etc., suitable for ingestion by the patient.

Medicaments for oral use can be obtained through combination of active compounds with solid excipient, optionally grinding a resulting mixture, and processing the mixture of granules, after adding suitable addition compounds, if desired, to obtain tablets or dragee cores. Suitable excipients are carbohydrate or protein fillers. These include, but are not limited to sugars, including lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins, such as gelatin or collagen. If desired, disintegrating or solubilizing agents may be added, such as the cross-linked polyvinyl pyrrolidone, agar, alginic acid, or a salt thereof, such as sodium alginate.

Dragee cores are provided with suitable coating such as concentrated sugar solutions, which may also contain gum arabic, talc, polyvinylpyrrolidone, carbopol gel, polyethylene, glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage).

Medicaments, which can be used orally, include push-fit capsules made of gelatin, as well as soft, sealed capsules made of gelatin and a coating such as glycerol or sorbitol. Push-fit capsules can contain active ingredients mixed with filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Medicaments for parenteral administration include aqueous solutions of active compounds. For injection, the medicaments of the invention may be formulated in aqueous solutions, preferably in physiologically compatible buffers such as Hank's solution, Ringer's solution, or physiologically buffered saline. Aqueous injection suspensions may contain substances, which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or lipsomes. Optionally, the suspension may also contain suitable stabilizers or agents, which increase the solubility of the compounds to allow for the preparation of highly concentrated solutions.

For topical or nasal administration, penetrants appropriate to the particular barrier to be permeated are used in the formulation. Such penetrants are generally known in the art.

Medicaments useful for treating mammalian subjects susceptible to bone fracture may be manufactured in a manner similar to that know in the art (e.g., by means of conventional mixing, dissolving, granulation, dragee-making, levigating, emulsifying, encapsulation, entrapping or lyophilizing processes). The medicaments may also be modified to provide appropriate releases characteristics, e.g., sustained release or targeted release, by conventional means e.g., coating.

The medicaments may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5, that is combined with buffer prior to use.

After such medicaments formulated in an acceptable carrier have been prepared, they can be placed in an appropriate container and labeled for treatment of an indicated condition.

Medicaments suitable for prevention or reduction of bone damage include compositions wherein the active ingredients are contained in an effective amount to achieve the intended purpose. The amount actually administered will be dependent upon the individual to which treatment is to be applied, and will preferably be an optimized amount such that the desired effect is achieved without significant side-effects. The determination of a therapeutically effective dose is well within the capability of those skilled in the art. Of course, the skilled person will realize that divided and partial doses are also within the scope of the invention.

For any compound, the therapeutically effective dose can be estimated initially either in cell culture assays or in any appropriate animal model (e.g., primate, rats and guinea pigs for hypertension and other small laboratory animals). These assays should take into account receptor activity as well as downstream processing activity. The animal model is also used to achieve a desirable concentration range and route of administration. Such information can then be used to determine useful doses and routes for administration in humans.

A therapeutically effective amount refers to that amount of agent, which ameliorates the symptoms or condition. Therapeutic efficacy and toxicity of such compounds can be determined by standard pharmaceutical procedures, in cell cultures or experimental animals (e.g., $ED_{50}$, the dose therapeutically effective in 50% of the population; and $LD_{50}$, the dose lethal to 50% of the population). The dose ratio between therapeutic and toxic effects is the therapeutic index, and it can be expressed as the ratio $ED_{50}/LD_{50}$. Medicaments, which exhibit large therapeutic indices, are preferred. The data obtained from cell culture assays and animal studies is used in formulating a range of dosage for human use. The dosage of such compounds lies preferably within a range of circulation concentrations that include the ED$_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Long acting medicaments might be administered every 3 to 4 days, every week, or once every two weeks depending on half-life and clearance rate of the particular formulation. Guidance as to particular dosages and methods for delivery is provided in the literature (see U.S. Pat. Nos. 4,657,760; 5,206,344 and 5,225,212, herein incorporated by reference).

In a third aspect of the present invention, there is provided a method of formulating a treatment regimen to decrease the risk of bone fracture. In some embodiments the method comprises analyzing nucleic acid molecules of a mammalian subject to determine the presence of the px haplotype of the ERα (haplotype 1) and the baT haplotype of the VDR gene (haplotype 1). This may be done according to the methods provided in the first aspect of the invention.

In a third aspect of the present invention, there is provided a method of formulating a treatment regimen to decrease the risk of bone fracture. In some embodiments the method comprises analyzing nucleic acid molecules and/or proteins of a mammalian subject to determine the presence of the px haplotype of the estrogen receptor a gene, wherein said haplotype is associated with risk of bone fracture, and formulating a treatment regimen to decrease the risk of bone fracture. The nucleic acid molecules can be analyzed using, for example, the techniques described in connection with the methods provided in the first aspect of the invention.

The effect of a therapeutic or preventative agent may depend on the underlying cause of the bone damage, in some cases it may be preferable to avoid the use of certain treatments for example, the presence or absence of particular alleles of a gene will provide a useful indication as to which is the most appropriate preventative measure. This aspect of the present invention may also be useful for identifying agents which may be used in the treatment of bone damage.

Thus, in some embodiments, the present invention provides methods for predicting the response of a mammalian subject to treatment to decrease the risk of bone damage that comprises the steps of: (1) determining which allele(s) of polymorphisms in an ERα gene, or the combination of an ERα gene and a VDR gene a mammalian subject has; and (2) predicting the response of the subject to treatment, wherein the absence of an allele of a polymorphism in an ERα gene or a VDR gene that is associated with an increased risk of bone damage is indicative that treatment of the mammalian subject is unlikely to reduce the risk of bone damage. The polymorphisms in the ERα gene that is associated with an increased risk of bone damage may be the C397T and or G351A polymorphisms. The polymorphisms in the VDR gene that are associated with an increased risk of bone damage may be the baT polymorphisms.

In some embodiments, the method comprises the steps of: (1) determining that a mammalian subject has an increased susceptibility to bone damage by using a method comprising the step of determining the presence in the subject of one or more allele(s) of polymorphisms in an ERα gene and a VDR gene that are associated with increased susceptibility to bone damage; and (2) predicting the response of the subject to treatment wherein the absence of an allele of a polymorphism in ERα that is associated with an increased risk of bone damage is indicative that treatment of the subject is unlikely to reduce the risk of bone damage. The polymorphism in the ERα gene that is associated with an increased risk of bone damage may be the C397T and/or the G351A polymorphisms. The polymorphism in the VDR gene that is associated with an increased risk of bone damage may be the baT polymorphism.

In a fourth aspect of the invention there is provided methods of determining susceptibility to bone fracture in a mammalian subject, wherein each method comprises the step of utilizing a kit to determine whether a px haplotype of an estrogen receptor a gene is present in a mammalian subject, wherein said kit comprises (i) one or more nucleic acid primer molecules for amplification of a portion of the estrogen receptor a gene, (ii) means for determining whether the px haplotype of said gene is present, and (iii) means for indicating a correlation between the presence of the px haplotype and risk of bone fracture, and wherein the presence of the px haplotype in the mammalian subject is indicative of susceptibility to bone fracture.

Some embodiments of the methods further comprise the step of determining whether a baT haplotype of a vitamin D receptor gene is present in the mammalian subject, said kit further comprising (i) one or more nucleic acid primer molecules for amplification of a portion of the vitamin D receptor gene, (ii) means for determining whether the baT haplotype of the vitamin D receptor gene is present, and (iii) means for indicating a correlation between the presence of the baT haplotype and risk of bone fracture.

Details of compounds of the Kit include those described below in relation to the fifth aspect.

The Method of the fourth aspect may be performed using any suitable methods known in the art, for example those as discussed above in relation to the method of the first aspect of the invention.

In a fifth aspect of the present invention, there is provided kits for use in determining which allele(s) of a polymorphism of an ERα gene or the combination of an ERα gene and a VDR gene are present in a mammalian subject. The kits include (i) one or more nucleic acid primer molecules for amplification of a portion of an estrogen receptor α gene, (ii) means for determining whether a px haplotype of said gene is present; and (iii) means for indicating a correlation between the presence of said haplotype and risk of bone fracture. In some embodiments the kits include (i) one or more nucleic acid primer molecules for amplification of a portion of a vitamin D receptor gene, (ii) means for determining whether a baT haplotype of the vitamin D receptor gene is present, and (iii) means for indicating a correlation between the presence of the baT haplotype and risk of bone fracture.

In some embodiments, the kit provides a method for determining susceptibility to bone damage by determining the presence of alleles of ERα or alleles of ERα and VDR that are associated with an increased or decreased susceptibility to bone damage. In further embodiments, the kit may be used in a method of predicting the response of a subject to treatment by determining the presence of alleles of ERα or alleles of ERα and VDR that are associated with an increased or decreased susceptibility to bone damage.

Preferably, the kit also comprises means for indicating a correlation between the allele(s) and risk of bone damage, or for predicting the response of a mammalian subject to treatment. Thus, the kit may contain written indicia providing information to the user for interpreting the results of the analysis. For example the written indicia may explain that the presence of the PvuII and XbaI restriction sites at the p and x polymorphisms of the ERα gene in a subject indicates the presence of the T and A alleles at these polymorphic sites.

Preferably, the primer molecules are suitable for amplification of at least a portion of the ERα gene or the ERα and VDR genes. Primers suitable for amplification of a portion of the ERα gene would be readily available to a person skilled in the art. Examples of suitable primers are described above. For example, suitable primers may amplify a fragment comprising a portion of the ERα gene, and determine which allele(s) of the C397T and G351A (px) polymorphisms in ERα is/are present. Examples of such primers include:

SEQ ID NO:3: 5'-GATATCCAGGGTTATGTGGCA-3'

SEQ ID NO:4: 5'-AGGTGTTGCCTATTATATTAACCTTGA-3'

Primers suitable for amplification of a portion of the VDR gene would also be readily available to a person skilled in the art. For example, suitable primers may amplify a portion of the VDR gene to determine which allele(s) of the baT polymorphisms of the VDR gene is present. Suitable primers include:

SEQ ID NO:5  5'-CAACCAAGACTACAAGTACCGCGTCAGTGA-3'
             and/or

SEQ ID NO:6  5'-TTTGGCTCCAATCAGATACATGGGA-3'

SEQ ID NO:7  5'-GCAACTCCTCATGGCTGAGGTCTC-3'

Means for determining which allele(s) is/are present in the ERα gene, and/or VDR gene may include any reagents or molecules necessary for use in any of the methods described above. For example, where PCR followed by DNA digestion is used, said means preferably include PCR reagents and one or more of the PvuII and/or XbaI restriction enzymes. Where the method employs Southern Blotting, heteroduplex visualization, or fluorescent labeling techniques for example, probes which bind to the appropriate region of the ERα gene, and/or VDR gene may be included. Where necessary, such probes may be labeled to allow detection, for example by nick-translation, radio- or fluorescent-labeling, or random primer extension whereby the non-labeled nucleotides serve as a template for the synthesis of labeled molecules. Other methods for labeling probes are well known in the art.

The means for correlating the allele present with risk of bone damage, or for predicting response to treatment, may be in the form of a chart or visual aid. The chart or visual aid may indicate that presence of the p and x alleles of the ERα gene and the baT alleles of the VDR gene is associated with increased risk of bone damage. In a preferred feature of the fifth aspect, the kit may also comprise control DNA samples, for comparison with DNA sequences of a subject. The control samples may comprise the sequence of one or more alleles of the ERα and/or VDR genes.

The following examples are provided for the purpose of illustration, not limiting, the present invention.

EXAMPLE 1

This Example describes the identification of polymorphisms in the ERα gene and the VDR gene that are positively correlated with increased susceptibility to bone fracture in human beings.

Study Subjects

All women included in this study were part of a population-based cohort study of subjects aged 55 years or more, living in the Ommoord district of the city of Rotterdam in The Netherlands. The objective of the study was to document the occurrence of disease in the elderly in relation to several potential determinants (1). A total of 10,275 persons were invited for baseline examination in 1990. Of those 7,983 (61.1% women) participated, bringing the overall response rate to 78%. The baseline assessments included the measurement of anthropometric characteristics, femoral and lumbar spine BMD. Subjects were excluded according to the following criteria: age 80 years and over, use of a walking aid, use of estrogen or hormone replacement therapy, diuretic, thyroid hormone or cytostatics, or known diabetes mellitus. After genotyping women with the rare VDR haplotypes 4 and 5 (n=16) were excluded. Anthropometric data, DNA samples and genotype data for both loci were finally available in a sample of 1062 women. Data on incident vertebral fractures were available for a subgroup of 634 women. The follow-up time was on average 6.5 (SD 0.4) years.

Measurements

At baseline height and weight were measured. BMD (in $g/cm^2$) was measured at the femoral neck and lumbar spine by dual energy X-ray absorptiometry (Lunar DPX-L densitometer), as reported earlier (2). Body mass index (BMI) was computed as weight in kilograms divided by height in square meters ($kg/m^2$). Age at menopause was assessed by questionnaire. Dietary intakes for calcium (mg/day) and vitamin D (mg/day) were assessed by food frequency questionnaire and adjusted for energy intake. Both at baseline, between 1990 and 1993 and at the follow-up visit, between 1997-1999, radiographs of the spine from the fourth thoracic to the fifth lumbar vertebrae were taken. All follow-up photos were analyzed for the presence of vertebral fractures by the McCloskey/Kanis method (3). The occurrence of non-vertebral fractures was recorded, confirmed and classified by a physician. In our study population 85 incident vertebral fractures were captured. 131 subjects had a non-vertebral fracture of which 6 had a prevalent vertebral fracture.

Determination of VDR and ERα Genotypes

Figure 2:
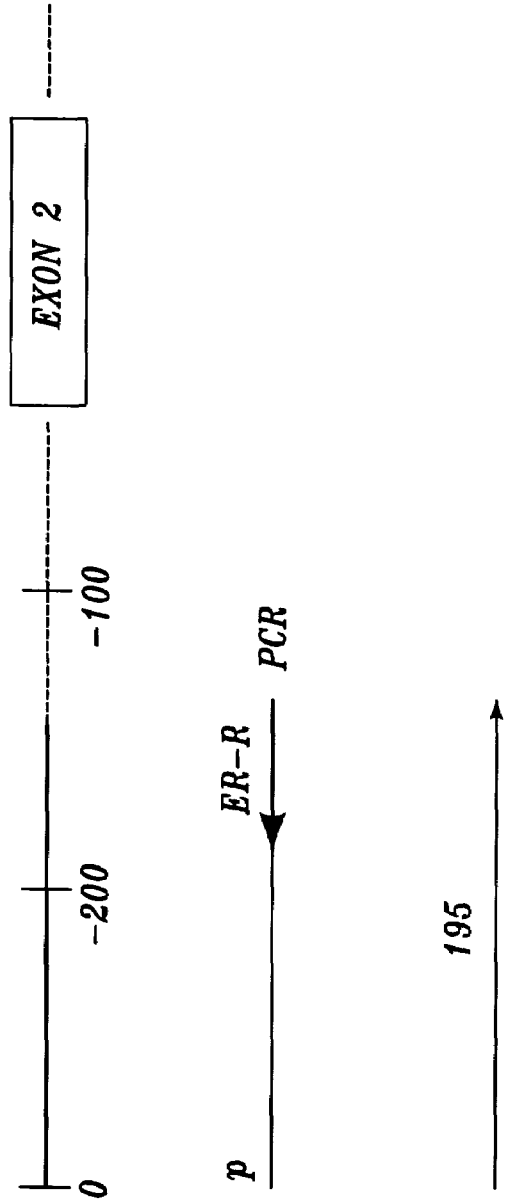
FIG. 2 shows ER gene: direct molecular haplotyping. For details see Example 1.
Figure 2:
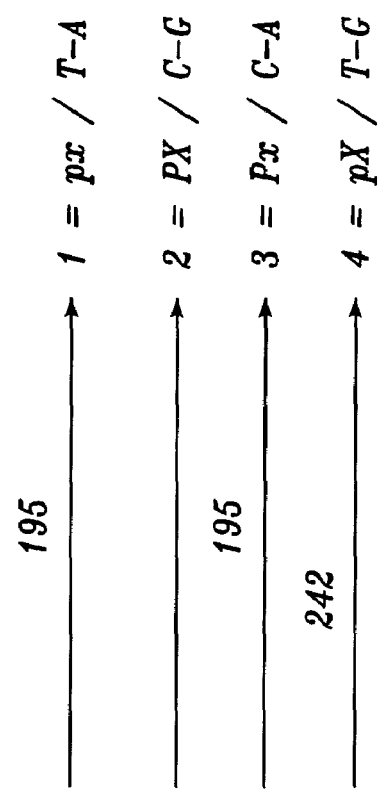

For genotyping we determined haplotypes of the BsmI, ApaI, and TaqI restriction fragment length polymorphisms (RFLPs) at the 3' end of the VDR gene and haplotypes of the PvuII- and XbaI RFLPs in the first intron of the ERα gene by direct molecular haplotyping methods as described previously (4). Three frequent VDR haplotypes were discerned, encoded 1 (baT), 2 (BAt), and 3 (bAT) (FIG. 1). The less frequent haplotypes 4 and 5 were excluded from the analysis (n=16). Women carrying these genotypes represent 1.5% of the population. For direct molecular haplotyping of the PvuII and XbaI RFLPs a 346 bp PCR fragment was generated by a forward primer (SEQ ID NO:3: 5'-GATATC-CAGGGT TATGTGGCA-3') and a reverse primer (SEQ ID NO:4: 5'-AGGTGTTGCCTATTATATTAACCTTGA-3') in a reaction mixture of 10 μL containing 20 ng of genomic DNA, 50 mM KCl, 10 mM Tris-HCl (pH 8.3), 1.5 mM $MgCl_2$, 0.2 mM deoxy-NTP, 2 pM of each primer, and 0.2 U Super Taq polymerase (HT Biotechnology Ltd., Cambridge, UK). The reactions were performed in 384-well format in a thermocycler (MJ-tetrad) with a cycling protocol of 94, 60 and 72 C for 45 seconds each for 30 cycles. Ten microliters of PCR product were digested by simultaneous addition of 5 μl of digestion mixture containing 5 U PvuII, 7 U XbaI restriction enzyme (MBI Fermentas) and 1.5 μL of ReactBuffer 2 (Life Technologies, Breda, The Netherlands) and incubating for 90 minutes at 37° C. The digestion products were analyzed by electrophoresis in a 3% agarose gel in 0.5×TBE (1×TBE=89 mM Tris, 89 mM boric acid, 2 mM $Na_2EDTA$) for 80 minutes at 125 Volts. Separation patterns were documented with a digital camera (DC120, Kodak Company, Rochester, N.Y., U.S.A.) under UV illumination (302 nm). Three ERα haplotype alleles were identified, encoded 1 (px/T-A), 2 (PX/C-G) and 3 (Px/C-A) combining to six genotypes 11, 12, 13, 22, 23 and 33 (FIG. 2). We did not observe the fourth possible haplotype (pX; −397int1T and −351int1G) in our population.

Statistical Analysis

Differences in mean age at baseline between the study group and the Rotterdam Study were evaluated by means of analysis of variance (ANOVA). All other differences in baseline characteristics were compared by analysis of covariance (ANCOVA) testing with age to adjust for possible confounding effects. Differences in baseline characteristics between the different genotype groups of the ERα gene were compared as follows. We grouped subjects by allele copy number (0,1,2) for the haplotype alleles of interest. We allowed for three possible models to explain differences between groups, i.e., an allele dose effect, a dominant effect or a recessive effect. Allele dose was defined as the number of copies of a certain allele in the genotype. In case of a consistent trend reflected as an allele dose effect, we performed a (multiple) linear or logistic regression analysis to quantify the association. In case of a dominant or recessive effect of the test-allele, ANOVA and ANCOVA tests were performed. For dominant effects we compared test-allele carriers versus non-carriers while for recessive effects, subjects homozygous for the test allele were compared to heterozygous carriers and non-carriers.

Odds ratios (ORs) with 95% confidence intervals (95% CI) were calculated by (multiple) logistic regression analyses to estimate the relative risk of fractures at baseline by genotypes of the risk allele, with no copies of the risk allele as the reference group. First, we calculated crude odds ratios, and, secondly, we adjusted for potentially confounding factors (age, BMI, BMD, and age at menopause). We used SPSS version 9.0 (SPSS Inc., Chicago, USA) for all our analyses.

Results

Baseline Characteristics

The study population (n=1062) was on average 67.0 (SD 6.9) years old, had a BMI of 26.1 (SD 3.7) $kg/m^2$, and age at menopause at 48.7 (SD 4.9) years. Dietary calcium and vitamin D intake were on average 1093 (SD 326) mg/day and 1.96 (SD 1.15) mg/day, respectively. Lumbar spine BMD was on average 1.01 (SD 0.17) $g/cm^2$ and femoral neck BMD was on average 0.81 (SD 0.12) $g/cm^2$, respectively. All women were independently living.

Table 1 shows allele and genotype frequencies for ERα and VDR polymorphisms. The genotype distribution was found to be in Hardy Weinberg equilibrium.

TABLE 1

Genotype and allele frequencies of ERα and VDR polymorphisms in the study population.

| ERα genotype | Number (%) | VDR genotype | Number (%) |
|---|---|---|---|
| 11 | 297 (28.0) | 11 | 271 (25.5) |
| 12 | 409 (38.5) | 12 | 401 (37.8) |
| 13 | 124 (11.7) | 13 | 105 (9.9) |
| 22 | 138 (13.0) | 22 | 183 (17.2) |
| 23 | 82 (7.7) | 23 | 89 (8.4) |
| 33 | 12 (1.1) | 33 | 13 (1.2) |
| Total | 1062 (100) | Total | 1062 (100) |
| p value HWE | 0.81 | p value HWE | 0.13 |
| 1 | 1127 (53.1) | 1 | 1048 (49.3) |
| 2 | 767 (36.1) | 2 | 856 (40.3) |
| 3 | 230 (10.8) | 3 | 220 (10.4) |
| Total | 2124 (100) | Total | 2124 (100) |

When we analyzed for known risk factors for osteoporosis by ERα and VDR genotypes, no differences were shown apart from ERα haplotype 1 (px) that appeared to be dose-dependently associated with later onset of menopause, as we have published earlier (Table 2). Similar data were found for the subgroup of 634 women participating in the analysis for vertebral fractures (data not shown).

TABLE 2

Characteristics of 1062 postmenopausal women according to ERα haplotype 1 (A) and VDR haplotype 1 (B).

A.

| | ERα haplotype 1[b] | | |
|---|---|---|---|
| | Reference | Heterozygotes | Homozygotes |
| Characteristic[a] | (n = 232) | (n = 533) | (n = 297) |
| Age (year) | 67.6 ± 7.1 | 66.9 ± 6.9 | 66.8 ± 6.9 |
| BMI (kg/m$^2$) | 26.2 ± 3.8 | 26.1 ± 3.5 | 26.1 ± 4.0 |
| Age at menopause (year) | 47.9 ± 5.1 | 48.7 ± 5.0 | 49.2 ± 4.6[c] |
| Dietary calcium intake (mg/day) | 1098 ± 364 | 1097 ± 319 | 1081 ± 306 |
| Dietary vitamin D intake (mg/day) | 2.04 ± 1.32 | 1.96 ± 1.08 | 1.89 ± 1.12 |

B.

| | VDR haplotype 1[b] | | |
|---|---|---|---|
| | Reference | Heterozygotes | Homozygotes |
| Characteristic[a] | (n = 285) | (n = 506) | (n = 271) |
| Age (year) | 66.6 ± 6.6 | 67.3 ± 7.0 | 67.0 ± 6.8 |
| BMI (kg/m$^2$) | 26.0 ± 3.4 | 26.2 ± 3.7 | 26.3 ± 4.1 |
| Age at menopause (year) | 48.9 ± 4.8 | 48.3 ± 5.1 | 49.0 ± 4.7 |
| Dietary calcium intake (mg/day) | 1078 ± 334 | 1104 ± 331 | 1086 ± 306 |
| Dietary vitamin D intake (mg/day) | 2.03 ± 1.26 | 1.91 ± 1.08 | 1.97 ± 1.17 |

[a]Data shown are means ± SD.
[b]Reference includes ERα or VDR genotypes 22, 23, and 33; heterozygotes include 12 and 13; homozygotes include 11
[c]p = 0.02 (allele-dose association, tested by linear regression analysis)

Association of ERα and VDR with BMD

In Table 3 women are grouped according to carrier status for the ERα and VDR haplotypes as homozygous carriers (consisting of genotype 11) and heterozygous carriers (including the genotypes 12 and 13) of the ERα haplotype I (px) and VDR haplotype 1 (baT), respectively, and women not carrying these haplotypes (reference group, including genotypes 22, 23 and 33).

(baT) (p=0.09 for the interaction term). In the subgroup of 634 women, in which data on incident vertebral fractures were available, similar associations were found (data not

TABLE 3

Lumbar spine (A) BMD and femoral neck (B) BMD (mean ± SD) according to combined ERα haplotype 1 genotype and VDR haplotype 1 genotype.

| ERα haplotype 1[a] | Total | Reference | Heterozygotes | Homozygotes | p-value |
|---|---|---|---|---|---|
| A | | VDR haplotype 1[a] | | | |
| Total | 1.01 ± 0.29 (1062)[c] | 1.00 ± 0.17 (285) | 1.02 ± 0.16 (506) | 1.02 ± 0.16 (271) | NS |
| Reference | 1.04 ± 0.17 (232) | 1.01 ± 0.16 (59) | 1.04 ± 0.16 (111) | 1.05 ± 0.16 (62) | NS |
| Heterozygotes | 1.02 ± 0.16 (533) | 1.00 ± 0.16 (134) | 1.02 ± 0.16 (260) | 1.03 ± 0.17 (139) | NS |
| Homozygotes | 0.99 ± 0.16 (297) | 0.99 ± 0.16 (92) | 1.01 ± 0.16 (135) | 0.95 ± 0.16 (70) | 0.05[d] |
| p value | 0.003[e] | NS | NS | <0.001[f] | 0.09[f] |
| B | | VDR haplotype 1[b] | | | |
| Total | 0.81 ± 0.23 (1062) | 0.80 ± 0.12 (285) | 0.81 ± 0.11 (506) | 0.81 ± 0.12 (271) | NS |
| Reference | 0.81 ± 0.11 (232) | 0.79 ± 0.12 (59) | 0.82 ± 0.12 (111) | 0.81 ± 0.11 (62) | NS |
| Heterozygotes | 0.81 ± 0.12 (533) | 0.80 ± 0.12 (134) | 0.80 ± 0.11 (260) | 0.82 ± 0.12 (139) | NS |
| Homozygotes | 0.80 ± 0.12 (297) | 0.81 ± 0.12 (92) | 0.80 ± 0.12 (135) | 0.78 ± 0.12 (70) | NS |
| p value | NS | NS | NS | NS | 0.13[g] |

Values are adjusted for age, BMI; p values as tested by ANCOVA
[a]Reference includes ERα genotypes 22, 23, and 33; heterozygotes include 12 and 13; homozygote includes 11.
[b]Reference includes VDR genotypes 22, 23, and 33; heterozygotes include 12 and 13; homozygote includes 11.
[c]number of women
[d]p = 0.02 for recessive association as analysed by ANCOVA.
[e]p = 0.001 for allele dose association as analysed by linear regression analysis
[f]p < 0.001 for allele dose association as analysed by linear regression analysis
[g]p-value for the interaction term ERα haplotype 1*VDR haplotype 1

ERα haplotype 1 was dose-dependently associated with decreased lumbar spine BMD corresponding with 0.1 SD per copy ERα haplotype 1 (Table 3A, first data column). No association was found with femoral neck BMD (Table 3B, first data column). ERα haplotype 2 (PX) was associated with increased lumbar BMD, corresponding with 0.1 SD per copy ERα haplotype 2 (data not shown). These associations did not change after adjustment for potential confounders such as age, BMI, and age at menopause. No associations were found between ERα haplotype 3 (Px) and lumbar spine or femoral neck BMD (data not shown). Based on these data ERα haplotype 1 (px) was considered as risk allele. In the sample of 634 women, in whom data on incident vertebral fractures were available, the association between ERα haplotype 1 (px) and lumbar spine BMD showed a similar trend (p=0.11).

Based on our previous analyses (5) we selected VDR haplotype 1 (baT) as risk allele. In the present study no association between VDR haplotype 1 (baT) and lumbar spine or femoral neck BMD was observed (Table 3A and B, first data rows).

Interaction of ERα and VDR Genotypes with Respect to BMD

When the association of ERα haplotype 1 (px) with BMD was analyzed according to the carrier status for VDR haplotype 1 (baT), there was a significant allele-dose effect of ERα haplotype 1 (px) being associated with decreased lumbar spine BMD only for women homozygous for VDR haplotype 1 (baT) (Table 3A, fourth data column; p<0.001). This association was not influenced by age, BMI, and age at menopause. When age, BMI, ERα genotype and VDR genotype were taken together in a multivariate regression model, there appeared to be a borderline significant interaction between ERα haplotype 1 (px) and VDR haplotype 1 shown). No interaction between ERα and VDR genotypes was found for femoral neck BMD (Table 3B; p=0.13 for the interaction term).

Association of ERα and VDR with Fracture

Analysis of the distribution of fractures in women according to the ERα genotyperevealed an overrepresentation of vertebral fractures in women carrying the ERα haplotype I (Table 4).

TABLE 4

Number of women with vertebral fractures according to ERα genotype.

| ERα genotype | No. with fracture/total no.(%) |
|---|---|
| 11 | 40/187 (21.4) |
| 12 | 26/236 (11.0) |
| 13 | 10/71 (14.1) |
| 22 | 3/79 (3.8) |
| 23 | 6/53 (11.3) |
| 33 | 0/8 (0) |
| $X^2$ | 19.2 |
| p value | 0.0002 |

FIG. 2 shows separately the distribution of vertebral fractures according to the ERα haplotype 1 (px) and VDR haplotype 1 (baT) status. Vertebral fractures were overrepresented in women carrying ERα haplotype 1 (px). This association appeared to be dose dependent with 6.4% in non-carriers of ERα haplotype 1 (px), 12% vertebral fractures (OR 1.9, 95% CI 0.9-4.1) in women heterozygous for ERα haplotype 1 and 21% vertebral fractures (OR 3.9, 95% CI 1.7-8.2) in women homozygous for ERα haplotype 1 (px). For women carrying ERα haplotype 2 (PX) there was an allele dose association with decreased vertebral fracture risk (p<0.001) while for ERα haplotype 3 (Px) no differences were observed (p=0.53) (data not shown).

Figure 3:
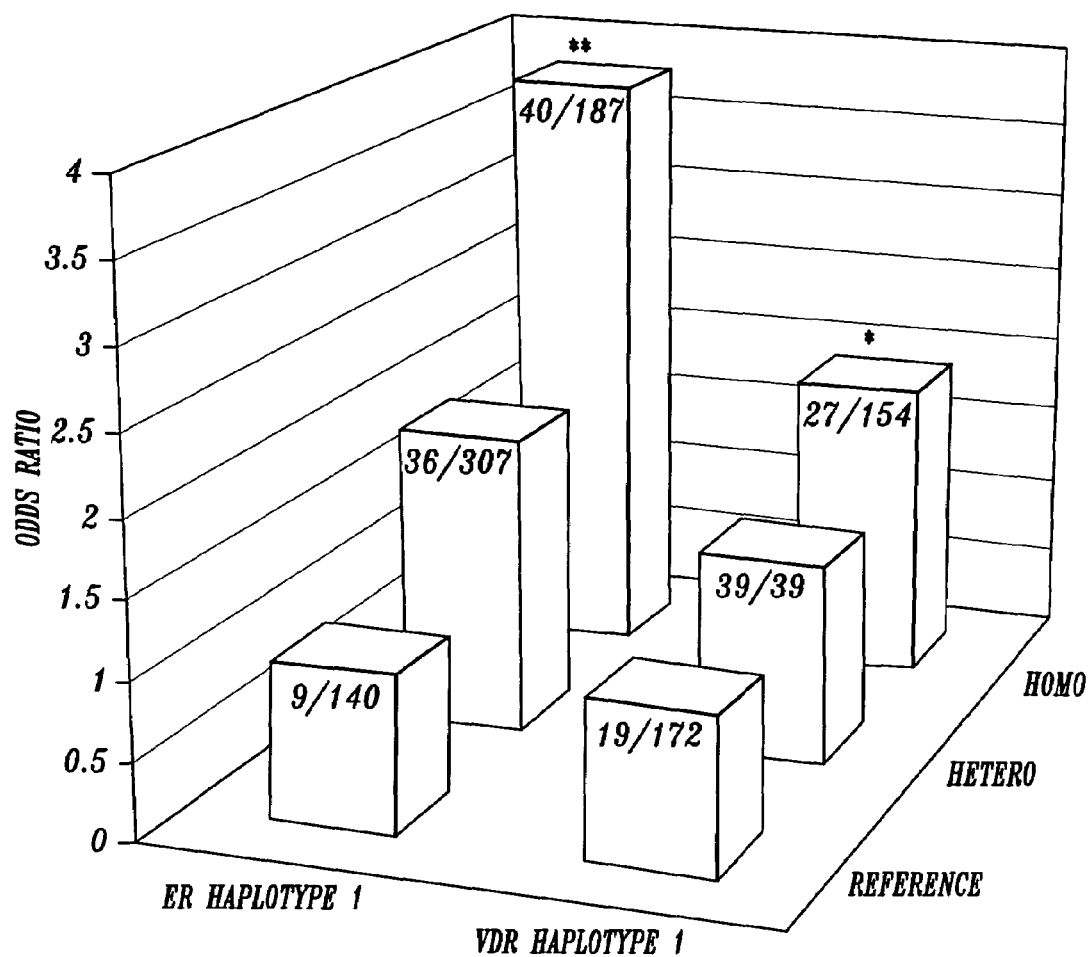
FIG. 3 shows odds ratios and numbers of vertebral fractures according to ERα haplotype 1 (px) and VDR haplotype 1 (baT) genotype. 'Reference' includes ERα and VDR genotypes 22, 23, and 33; 'hetero' includes 12 and 13 genotypes; 'homo' includes 11 genotype. **p-value<0.001 for allele dose association of ERα haplotype 1. *p-value=0.06 for allele dose association of VDR haplotype 1.

In a previous study VDR haplotype 1 (baT) was found to be associated with increased fracture risk (5). When women were grouped by VDR haplotype 1 (baT) genotype also an allele dose association was observed (FIG. 3). Non-carriers of VDR haplotype 1 had 11% vertebral fractures, women heterozygous for VDR haplotype 1 had 13% vertebral fractures (OR 1.3, 95% CI 0.7-2.3), while women homozygous for VDR haplotype 1 had 18% fractures (OR 1.9, 95% CI 1.0-3.7). VDR haplotypes 2 (BAt) and 3 (bAT) were not associated with vertebral fracture risk (data not shown).

No differences between the various ERα and VDR haplotypes were found when the risk for incident non-vertebral fractures was analyzed (data not shown).

Interaction of ERα and VDR with Respect to Fracture Risk

Figure 4:
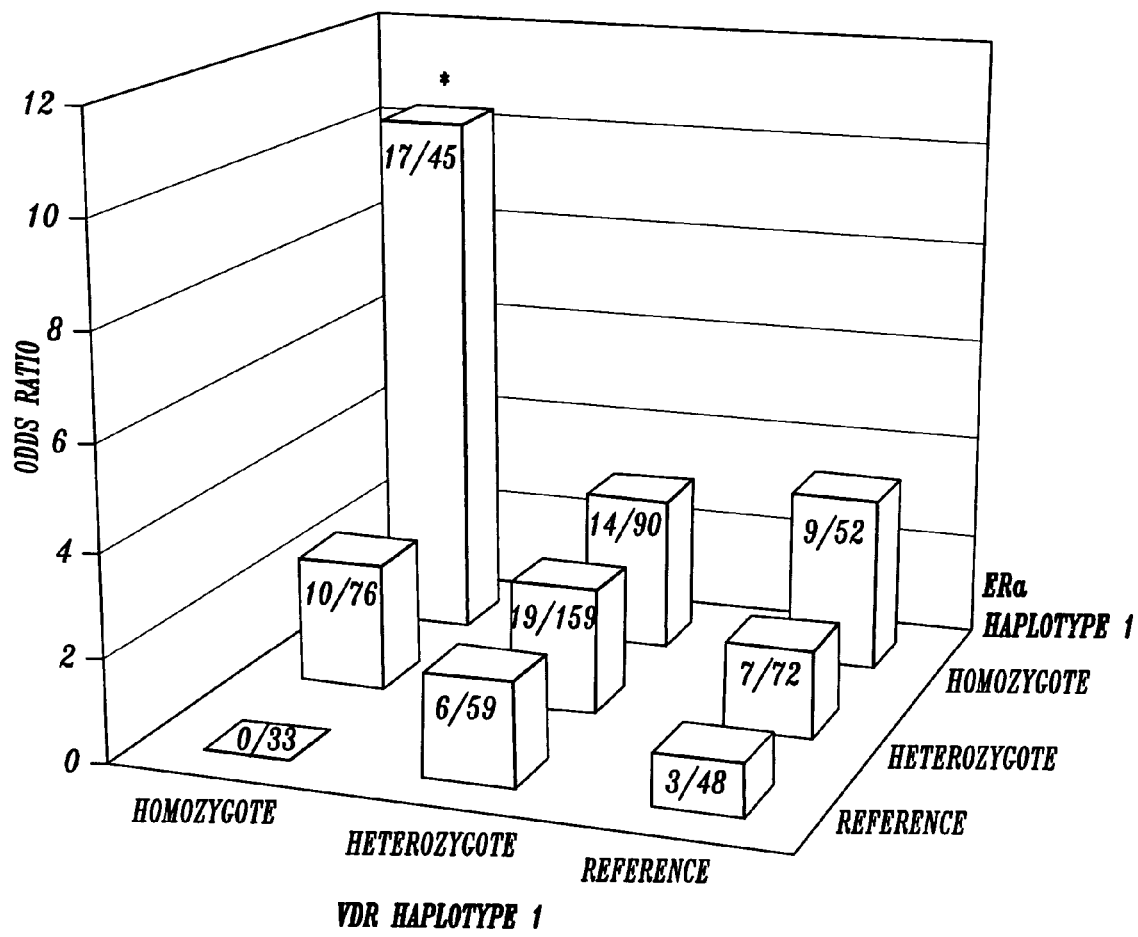
FIG. 4 shows odds ratios compared to the 'double reference' group and numbers of vertebral fractures according to combined ERα and VDR genotypes. 'Reference' includes ERα and VDR genotypes 22, 23, and 33; 'heterozygotes' include 12 and 13; 'homozygote' includes 11. *p-value<0.001 for allele dose association of ERα haplotype 1 (px) in VDR haplotype 1 (baT) homozygous carriers. p=0.01 for the interaction term.

When we further stratified by VDR haplotype 1 (baT) genotype we observed the ERα haplotype 1 (px) association to be modified by VDR haplotype 1 (baT) genotype (FIG. 4). Significant ERα haplotype 1 (px) genotype dependent differences were only observed in women homozygous for VDR haplotype 1 (baT). Logistic regression analysis showed that, compared to the 'double reference' group, within the group of VDR genotype [1,1] women have a 2-fold (95% CI 0.5-7.9) and 10-fold (95% CI 2.7-38) increased risk for vertebral fractures when being heterozygous or homozygous for ERα haplotype 1 (px), respectively. In non-carriers and heterozygous carriers of VDR haplotype 1 (baT) no significant ERα haplotype 1 (px) genotype dependent differences were observed. When age, BMI, ERα genotype, and VDR genotype were taken together in a multivariate regression model, there appeared to be a significant interaction between ERα haplotype 1 (px) and VDR haplotype 1 (baT) (p=0.01 for the interaction term). After adjustment for lumbar spine BMD and age at menopause the results did not change (data not shown).

Discussion

The data presented herein demonstrates for the first time interaction of polymorphisms in the VDR and ERα gene in relation to the risk of incident vertebral fracture risk. Women homozygous for both the VDR haplotype 1 (baT) and ERα haplotype 1 (px) had a 10-times higher vertebral fracture risk than non-carriers and a 3-4 times higher risk than carriers of either one of the risk haplotypes.

So far most association studies focused on single genes. Two meta-analyses showed a weak association of VDR genotypes with BMD, which supported our own findings in a sample of 2000 men and women from the Rotterdam study. A recent meta-analysis showed an association between ERα genotypes and lumbar and femoral BMD (6). Most genetic association studies for osteoporosis have been performed with BMD as endpoint while the clinically more relevant endpoint of osteoporosis is fracture. A limited number of studies have yet been able to address the association of specific gene polymorphisms with fractures. Previously we have shown that VDR haplotype 1 (baT) is the risk allele for osteoartiritis, vertebral and nonvertebral fractures (5, 7). Ioannidis et al. showed in a meta-analysis that the XbaI polymorphism and not the PvuII polymorphism was associated with increased combined risk for vertebral and non-vertebral fractures (6). In the present study direct haplotyping methods were used to increase genetic resolution. An association of ERα haplotype 1 (px) with lumbar spine BMD and vertebral fracture risk was demonstrated. Also at the lumbar spine a synergistic interaction between ERα and VDR genotype for BMD and fractures was detected. No interaction effect between ERα and VDR genotypes was found for femoral neck BMD and non-vertebral fracture risk. This is in line with previous data, which show a higher response to hormonal replacement therapy at the lumbar spine in contrast to the femoral neck. The ERα effect may be more pronounced in the spine, which contains more trabecular bone resulting in a higher rate of bone turnover compared to cortical bone, as present for example in the femoral neck.

We and others previously observed that ERα genotype is associated with differences in age at menarche and age at menopause. However, in our current analyses age of menopause did not influence the interaction we observed. This suggests that differences in the age of menopause are small and do not explain the interaction. However, because of the relatively small effect, such influences might only be observed in studies of sufficient power.

An interesting observation was that the association of both ERα and VDR genotypes with vertebral fracture incidence was independent of BMD. This indicates the significance of other bone characteristics for the risk of fracture. But it also pointed to the involvement of ERα and VDR genes in pathways (e.g., bone matrix synthesis and bone turnover) other than those directly reflected in BMD, and which also determine strength of bone and thereby fracture risk. For example, estrogen deficiency may increase the numbers of remodelling sites and deeper resorption lacunae and therefore produce loss of connectivity and increased risk for fractures.

A limitation of the present study may be health selection bias. However, genotype and allele frequencies are similar to those observed in other Caucasian study populations and so "Health" (apart from the risk for fractures) seems not to be genotype dependent and, therefore, we do not expect this to influence the results. Furthermore, potential selection bias was avoided by deriving cases and non-cases from the same source population.

An aspect that should be realised is that the polymorphisms in the ERα and VDR are anonymous. There is no direct known functional consequence for the ERα and VDR protein. Therefore, when association is found it is assumed that allele(s) of these single nucleotide polymorphisms are in linkage disequilibrium with one or more of the truly functional polymorphisms elsewhere in the gene. These functional polymorphisms could alter VDR or ERα protein structure or might affect the activity of the VDR and ERα 5' promoter and 3' UTR, leading to the expression of altered quantities of VDR47 and ERα proteins under physiologic conditions. Differential transcriptional activity of the VDR and ERα receptor proteins could then preferentially modulate subsets of target genes in vitamin D and estrogen responsive pathways.

Although the mechanism(s) for the gene-gene interaction we observe is so far unknown, it is conceivable from a physiological point of view. $1,25\text{-}(OH)_2D_3$ is an important factor in estrogen biosynthesis and might thus influence local equilibrium between estrogens and androgens. Furthermore $1,25\text{-}(OH)_2D_3$ regulates ER expression in osteoblast-like cells. In this way $1,25\text{-}(OH)_2D_3$ might regulate the effect of $E_2$ on bone metabolism. In vitro and in vivo studies have shown that several biological responses to treatment with vitamin D, such as intestinal calcium absorption and osteocalcin production, are VDR genotype dependent. If $1,25\text{-}(OH)_2D_3$ influences the effect of $E_2$ on bone metabolism, this effect might also be VDR genotype dependent.

On the other hand, $E_2$ influences vitamin D metabolism and VDR expression. Sex hormone replacement therapy increases total and free serum $1,25\text{-}(OH)_2D_3$ levels. In human fetal osteoblasts $E_2$ upregulates VDR expression.

Also in rat duodenal mucosa E$_2$ increases VDR expression and bioresponse. In this way E$_2$ might influence vitamin D regulated processes, like intestinal calcium absorption and osteocalcin production in bone. Several studies have demonstrated that the response to hormonal replacement therapy is ERα genotype dependent. Therefore, the effect of estrogen replacement on vitamin D regulated processes might also be ERα genotype dependent.

In conclusion, the present study shows an interlocus interaction in relation to BMD and fractures between two important candidate genes in osteoporosis. Recently, we also demonstrated an interaction between VDR and another candidate gene, the COLIA1 gene, with respect to fracture risk (5). Together, these findings underscore the multigenic character of osteoporosis and the importance of the contribution of gene interactions in determining fracture risk. At the same time our findings highlight the necessity of large (multicenter) studies to achieve sufficient statistical power to further elucidate the complex, multigenic character of osteoporosis.

While the preferred embodiment of the invention has been illustrated and described, it will be appreciated that various changes can be made therein without departing from the spirit and scope of the invention.

REFERENCES

1. Hofinan, A., Grobbee, D. E., de Jong, P. T. V. M., van den Ouweland, F. A. 1991 Determinants of disease and disability in the elderly: The Rotterdam Elderly Study, *Eur J Epidemiol* 7:403-422.
2. Willing, M., Sowers, M., Aron, D., Clark, M. K., Burns, T., Bunten, C., Crutchfield, M., D'Agostino, D., Jannausch 1998 Bone mineral density and its change in white women: estrogen and vitamin D receptor genes and their interaction, *J. Bone Miner Res.* 13:695-705.
3. Van der Klift, M., de Laet, C. E. D. H., McCloskey, E. V., Hofinan, A., Pols, H. A. P. 2002 The incidence of vertebral fractures in men and women: The Rotterdam Study, *J. Bone Miner Res.* 17:1051-1056.
4. Uitterlinden, A. G., Pols, H. A. P., Burger, H., Huang, Q., van Daele, P. L. A., van Duijn, C. M., Hofman, A., Birkenhäger, J. C., van Leeuwen, J. P. T. M. 1996 A large scale population based study of the association of vitamin D receptor gene polymorphisms with bone mineral density, *J. Bone Miner Res.* 11: 1242-1248.
5. Uitterlinden, A. G., Weel, A. E. A. M., Burger, H., Fang, Y., van Duyn, C. M., Hofman, A., van Leeuwen, J. P. T. M., Pols, H. A. P., 2001 Interaction between the vitamin D receptor gene and collagen type Iα1 gene in susceptibility for fracture, *J. Bone Miner Res.* 16:379-385.
6. Ionnannidis, J. P. A., Stavrou, I., Trikalinos, T. A., Zois, C., Luisa Brandi, M., et al. 2002 Association of polymorphisms of the estrogen receptor α gene with bone mineral density and fracture risk in women: a meta-analysis, *J. Bone Min. Res.* 17:2048-2060.
7. Uitterlinden, A. G., Burger, H., Huang, Q., Odding, E., van Duijn, C. M., Hofinan, A., Birkhanger, J. C., van Leeuwen, J. P. T. M., Pols, H. A. P. 1997 Vitamin D receptor genotype is associated with radiographic osteoarthritis at the knee, *J. Clin. Invest.* 100:259-263.

The embodiments of the invention in which an exclusive property ot priviledge is claimed are defined as follows:

1. A method of determining susceptibility to vertebral bone mineral density (BMD)-independent fracture in a Caucasian female subject, the subject comprising:
   (i) at least one estrogen receptor α gene comprising a PvuII site and a XbaI site, wherein the PvuII site can exist as a P or p allelic form, and the XbaI site can exist as an X or x allelic form; and
   (ii) a vitamin D receptor gene, wherein the vitamin D receptor gene comprises a BsmI site, an ApaI site and a TaqI site, wherein the BsmI site can exist as a B or b allelic form, the ApaI site can exist as an A or a allelic form, and the TaqI site can exist as a T or t allelic form, said method comprising analyzing nucleic acid molecules obtained from the subject to determine which of the P, p, X, and x alleles of the estrogen receptor α gene are present, and further comprising determining the copy number of a member of the group consisting of the B, b, A, a, T and t alleles of the vitamin D receptor gene, wherein the presence of a haplotype comprising the p and x alleles of the estrogen receptor a gene and a homozygous haplotype comprising the baT alleles of the vitamin D receptor gene is indicative of an increased susceptibility to vertebral BMD-independent fracture.

2. A method according to claim 1, wherein said method is performed on a blood or tissue sample of the subject.

3. The method of claim 1 wherein the subject is suffering from low bone mineral density.

4. The method of claim 1 wherein the subject has a normal level of bone mineral density.

5. A method of treating a Caucasian female subject to reduce the risk of vertebral bone mineral density (BMD)-independent fracture, wherein the subject comprises:

(i) at least one estrogen receptor α gene comprising a PvuII site and a XbaI site, wherein the PvuII site can exist as a P or p allelic form, and the XbaI site can exist as an X or x allelic form; and (ii) a vitamin D receptor gene, wherein the vitamin D receptor gene comprises a BsmI site, an ApaI site and a TaqI site, wherein the BsmI site can exist as a B or b allelic form, the ApaI site can exist as an A or a allelic form, and the TaqI site can exist as a T or t allelic form, wherein the presence of a haplotype comprising the p and x alleles of the estrogen receptor gene and a homozygous haplotype comprising the baT alleles of the vitamin D receptor gene is indicative of an increased susceptibility to vertebral BMD-independent fracture, said method comprising determining whether the px haplotype of the estrogen receptor α gene and the homozygous baT haplotype of the vitamin D receptor gene are present in said subject, and treating the subject to reduce the risk of vertebral BMD-independent fracture if the subject has both said haplotypes, wherein the treatment comprises at least one treatment selected from the group consisting of modifications to lifestyle, regular exercise, changes in diet and administration of a pharmaceutical preparation effective to reduce the risk of vertebral BMD-independent fracture.

6. A method according to claim 1, wherein the presence of the px haplotype is determined by amplification of a portion of the first intron of the estrogen receptor α gene to yield an amplified fragment, followed by restriction enzyme digestion of the amplified fragment.

7. A method according to claim 1, wherein the presence of the baT haplotype of the vitamin D receptor gene is determined by amplification of a portion of the vitamin D receptor gene between exon 7 and the 3' untranslated region to yield an amplified fragment, followed by restriction enzyme digestion of the amplified fragment.

* * * * *